United States Patent [19]

Hazato et al.

[11] Patent Number: 4,711,895

[45] Date of Patent: Dec. 8, 1987

[54] 4-HYDROXY-2-CYCLOPENTENONE, PROCESS FOR PRODUCTION THEREOF, PHARMACEUTICAL COMPOSITION COMPRISING IT

[75] Inventors: Atsuo Hazato; Satsohi Sugiura, both of Hino; Seizi Kurozumi, Kokubunji; Ryoji Noyori, Aichi, all of Japan

[73] Assignee: Teijin Limited, Osaka, Japan

[21] Appl. No.: 791,156

[22] Filed: Oct. 22, 1985

[30] Foreign Application Priority Data

Oct. 22, 1984 [JP] Japan .................. 59-220475
Oct. 22, 1984 [JP] Japan .................. 59-220476
Feb. 18, 1985 [JP] Japan .................. 60-28429
Jun. 18, 1985 [JP] Japan .................. 60-130845

[51] Int. Cl.$^4$ .................................. A61K 31/19
[52] U.S. Cl. .................................. 514/530; 514/573; 514/690; 514/684; 568/379; 568/380; 568/375; 568/376; 568/330; 558/441; 560/121; 560/122; 560/231; 560/255; 562/503; 562/504
[58] Field of Search ............... 508/379, 380; 568/330, 568/379, 380, 375, 376; 560/121, 122, 231, 255; 562/503, 504; 514/530, 573, 690, 684; 558/441

[56] References Cited

U.S. PATENT DOCUMENTS 4,560,703 12/1985 Fukushima et al. .......... 560/121

FOREIGN PATENT DOCUMENTS 0131441  1/1985  European Pat. Off. ....... 560/121
59-184159  1/1984  Japan .................. 560/121
59-59646   6/1984  Japan .................. 560/121
60-4129    7/1985  Japan .................. 560/121
WO85/3706  8/1985  PCT Int'l Appl. ......... 560/121

OTHER PUBLICATIONS

Monthly Drugs & Medical Inst., vol. 24, pp. 37-4/1982).

Primary Examiner—James H. Reamer
Attorney, Agent, or Firm—Wenderoth, Lind & Ponack

[57] ABSTRACT

A 4-hydroxy-2-cyclopentenone represented by the following formula (I)

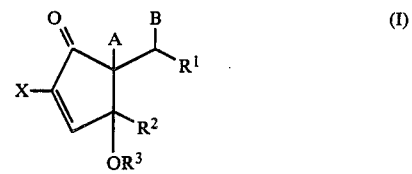

wherein X represents a hydrogen or halogen atom, A represents a hydrogen atom and B represents a hydroxyl group, or A and B are bonded to each other to represent a bond, $R^1$ represents a substituted or unsubstituted alkyl, alkenyl or alkynyl group having 1 to 10 carbon atoms, $R^2$ represents a substituted or unsubstituted alkyl, alkenyl or alkynyl group having 1 to 10 carbon atoms, and $R^3$ represents a hydrogen atom or a protective group for a hydroxyl group, provided that $R^2$ is not a 2-octenyl, 8-acetoxy-2-octenyl or 2,5-octadienyl group. The compounds of formula (I) in which A is hydrogen and B is hydroxyl group are prepared by subjecting a 5-unsubstituted cyclopentenone and an aldehyde to aldol condensation reaction. The compounds of formula (I) in which A and B form a bond is prepared by subjecting the compounds of the formula (I) in which A is hydrogen and B is hydroxyl group to dehydration. The compounds (I) are useful for treatment of malignant tumors.

9 Claims, No Drawings

4-HYDROXY-2-CYCLOPENTENONE, PROCESS FOR PRODUCTION THEREOF, PHARMACEUTICAL COMPOSITION COMPRISING IT

This invention relates to a 4-hydroxy-2-cyclopentenone, a process for production thereof, and to a pharmaceutical composition comprising it.

Prostaglandins are useful naturally occurring substances which have unique biological activities such as platelet aggregation inhibiting action and hypotensive action and have recently been used as agents for peripheral circulatory diseases in medical therapy. Prostaglandins A are known to be prostaglandins having a double bond at the cyclopentane ring, and for example, prostaglandin $A_2$ is expected to be useful as a drug having hypotensive activity [see E. J. Corey et al., J. Amer. Chem. Soc., 95, 6831 (1973)].

It has been reported that because prostaglandins A strongly inhibit DNA synthesis, they have a possibility of being usable as an antitumor agent [see Biochem. Biphys. Res. Commun., 87, 795, 1979; W. A. Turner et al., Prostaglandins Relat. Lipids, 2, 365–8 (1982)].

European Laid-Open Patent Application No. 0106576 (laid-open on April 25, 1984) describes 4,5-disubstituted-2-cyclopentenone selected from the group consisting of 5-alkylidene-4-substituted-2-cyclopentenones represented by the following formula

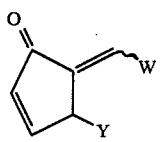

wherein W represents an aliphatic hydrocarbon group having 1 to 12 carbon atoms which may have a substituent, and Y represents an aliphatic hydrocarbon group having 1 to 12 carbon atoms which may have a substituent, and 5-(1-hydroxy-aliphatic hydrocarbon)-4-substituted-2-cyclopentenones represented by the following formula

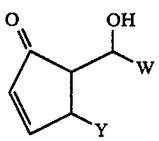

wherein W and Y are as defined for the above formula, which includes prostaglandins A, and states that these compounds are effective against malignant tumors.

European Laid-Open Patent Application No. 0131441 (laid-open on Jan. 16, 1985) discloses 5-alkylidene-2-halo-4-substituted-2-cyclopentenone represented by the following formula:

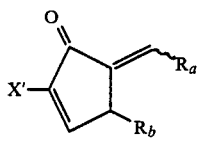

wherein $R_a$ represents a substituted or unsubstituted aliphatic hydrocarbon group having 1 to 12 carbon atoms or a substituted or unsubstituted phenyl group, $R_b$ represents a substituted or unsubstituted aliphatic hydrocarbon group having 1 to 12 carbon atoms, and X' represents a halogen atom, and states that these compounds are likewise effective against malignant tumors.

It is also known that prostaglandins D and J which differ from the prostaglandins A, are useful as antitumor agents [Japanese Laid-Open Patent Publication No. 216155/1983 and Proc. Natl. Acad. Sci., U.S.A. 81, 1317–1321).

It is known that a compound which is analogous to prostaglandin and is represented by the following formula

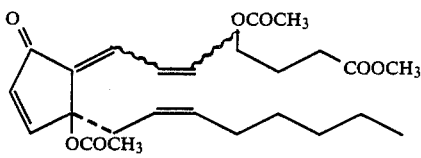

was isolated from Okinawan soft coral (*Clavularia viridis*), and it has such physiological activities as anti-inflammatory activity and anti-cancer activity [see H. Kikuchi et al., Tetrahedron Letters, 23, 5171 (1982); M. Kobayashi et al., Tetrahedron Letters, 23, 5331 (1982); and Masanori Fukushima, "Cancer and Chemotherapy", 10, 1930 (1983)].

Japanese Laid-Open Patent Publication No. 59646/1984 discloses that clavulone derivatives represented by the following formula

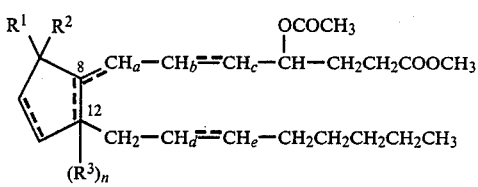

wherein $R^1$ and $R^2$ together represent a keto group, or one of them is a hydrogen atom and the other is a hydroxyl group, $R^3$ represents a hydrogen atom or an acetoxy group, n is 0 or 1, and when a double bond exists between the 8- and 12-positions, n is 0, a, b, c, d and e are each 1 or 2, and the dotted line shows that the above C—C bond is either single or double, and their utility as an anti-inflammatory agent.

Japanese Laid-Open Patent Publication No. 184158/1984 discloses clavulone derivatives represented by the following formula

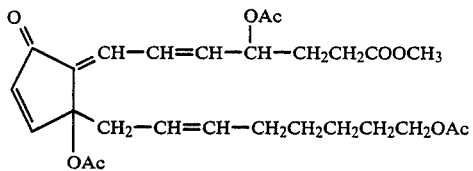

wherein Ac represents an acetyl group.

Japanese Laid-Open Patent Publication No. 4129/1985 discloses that clavulone derivatives within the two formulae given above are useful as antitumor agents.

E. J. Corey synthesized a clavulone derivative of the following formula

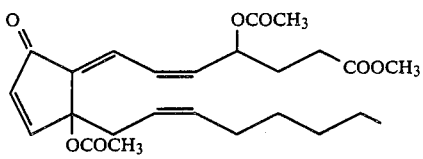

(J. Am. Chem. Soc., 106, 3384, 1984).

Likewise, H. Nagaoka et al. synthesized a clavulone derivative of the following formula

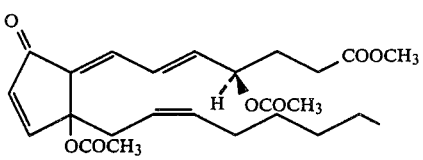

(Tetrahedron Letters, vol. 25, No. 33, pages 3621–3624, 1984).

Recently, punaglandins 1 and 2 represented by the following formulae

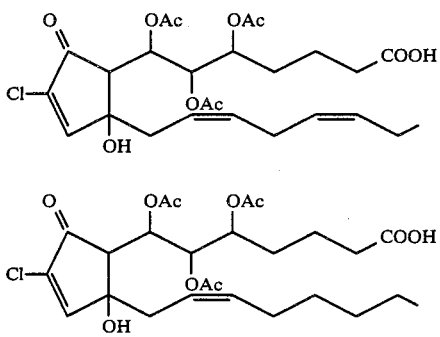

were isolated from *Telesto riisei* adhering to a ship's bottom which was taken at Oahu Island (Gekkan Yakuji, or Monthly Drugs and Medical Instruments, vol. 24, No. 6, pages 37–43, 1982).

PCT Patent Application Laid-Open WO85-03706 (laid-open on Aug. 29, 1985) describes punaglandins of the following formula

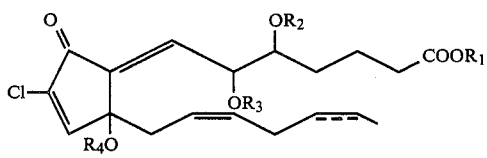

wherein $R_1$ represents a hydrogen atom, a $C_1$–$C_{10}$ alkyl group, or one equivalent of cation; $R_2$, $R_3$, and $R_4$ are identical or different and each represents a hydrogen atom or a $C_2$–$C_{10}$ acyl group; and the symbol ═ indicate a single bond or a double bond, and their usefulness for the treatment of malignant tumors.

Masanori Fukushima et al. reported that a compound of the following formula

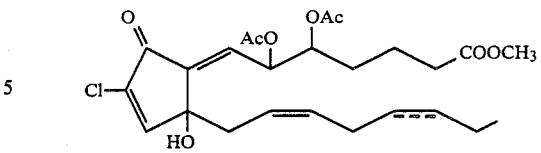

which is embraced within the formula given in the above PCT publication has anti-cancer activity [see Masanori Fukushima et al., Summary of Papers at the 43rd Conference of Japan Cancer Society, 909 (1984)].

It is an object of this invention to provide novel 4-hydroxy-2-cyclopentenones such as novel synthesized clavulones or punaglandins.

Another object of this invention is to provide 4-hydroxy-2-cyclopentenone having marked antitumor activity.

Still another object of this invention is to provide novel 4-hydroxy-2-cyclopentenones which differ from known natural clavulones or punaglandins in the omega-chain and exhibit antitumor activity equivalent to, or higher than, the known natural clavulones or punaglandins.

Yet another object of this invention is to provide novel 4-hydroxy-2-cyclopentenones which exhibit such pharmacological activities as antiviral activity or antimicrobial activity in addition to antitumor activity.

A further object of this invention is to provide a process for producing the novel-4-hydroxy-2-cyclopentenones of the invention.

A still further object of this invention is to provide a pharmaceutical composition comprising a 4-hydroxy-2-cyclopentenone in accordance with this invention as an active ingredient by utilizing its pharmacological activities described above.

An additional object of this invention is to provide cyclopentenones or cyclopentenols useful as starting materials for the production of the 4-hydroxy-2-cyclopentenones of this invention.

Other objects of this invention along with its advantages will become apparent from the following description.

These objects and advantages are achieved firstly by a 4-hydroxy-2-cyclopentenone represented by the following formula (I)

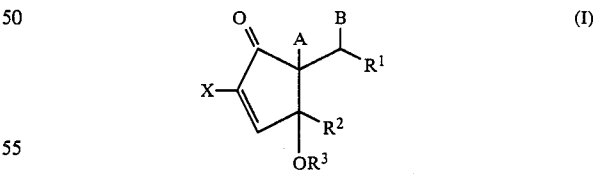

wherein X represents a hydrogen or halogen atom, A represents a hydrogen atom and B represents a hydroxyl group, or A and B are bonded to each other to represent a bond, $R^1$ represents a substituted or unsubstituted alkyl, alkenyl or alkynyl group having 1 to 10 carbon atoms, $R^2$ represents a substituted or unsubstituted alkyl, alkenyl or alkynyl group having 1 to 10 carbon atoms, and $R^3$ represents a hydrogen atom or a protective group for a hydroxyl group, provided that $R^2$ is not a 2-octenyl, 8-acetoxy-2-octenyl or 2,5-octadienyl group.

In formula (I), X represents a hydrogen or halogen atom. Examples of the halogen atom are fluorine, chlorine, bromine and iodine. Chlorine is preferred.

A represents a hydrogen atom and B represents a hydroxyl group, or A and B are bonded to each other to represent a bond. When A and B are bonded to each other to represent a bond, the above formula (I) represents 4-hydroxy-2-cyclopentenones represented specifically by the following formula (I)-a

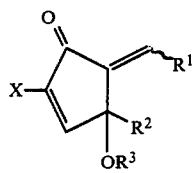

(I)-a wherein X, $R^1$, $R^2$ and $R^3$ are as defined with regard to formula (I).

When A is a hydrogen atom and B is a hydroxyl group, the above formula (I) represents 4-hydroxy-2-cyclopentenones represented specifically by the following formula (I)-b

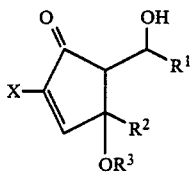

(I)-b wherein X, $R^1$, $R^2$ and $R^3$ are as defined in formula (I).

In formula (I), $R^1$ represents a substituted or unsubstituted alkyl, alkenyl or alkynyl group having 1 to 10 carbon atoms. It may be linear or branched.

Examples of the unsubstituted alkyl group include methyl, ethyl, n-propyl, iso-propyl, n-butyl, sec-butyl, tert-butyl, n-pentyl, n-hexyl, n-heptyl, n-octyl, n-nonyl and n-decyl.

Examples of the unsubstituted alkenyl group include ethenyl, 1-propen-1-yl, 2-propen-1-yl, 1-buten-1-yl, 1,3-butadien-1-yl, 2-buten-1-yl, 1-penten-1-yl, 2-penten-1-yl, 1-hexen-1-yl, 2-hexen-1-yl, 1,5-hexadien-1-yl, 3-hexen-1-yl, 1-hepten-1-yl, 1-octen-1-yl, 1,7-octadien-1-yl, 1-nonen-1-yl and 1-decen-1-yl.

Examples of the unsubstituted alkynyl group include ethynyl, 1-propyn-1-yl, 2-propyn-1-yl, 1butyn-1yl, 3-buten-1-yne-1-yl, 2-butyn-1-yl, 1-pentyn-1-yl, 2-pentyn-1-yl, 1-hexyn-1-yl, 2-hexyn-1-yl, 5-hexen-1-yne-1-yl, 3-hexyn1-yl, 1-heptyn-1-yl, 1-octyn-1-yl, 7-octen-1-yne-1-yl, 1-nonyn-1-yl and 1-decyn-1-yl.

These alkyl, alkenyl and alkynyl groups may have substituents.

Examples of the substituents include groups of the formula —$COOR^4$ (wherein $R^4$ represents a hydrogen atom, an alkyl group having 1 to 10 carbon atoms or one equivalent of a cation); groups of the formula —$OR^5$ (wherein $R^5$ represents a hydrogen atom, a $C_{1-6}$ alkyl which may be substituted by a halogen atom, a $C_{1-C7}$ carboacyl group, or a phenyl group which may be substituted by a halogen atom, an alkyl group having 1 to 4 carbon atoms or an alkoxy group having 1 to 4 carbon atoms); a phenyl group which may be substituted by a halogen atom, an alkyl group having 1 to 4 carbon atoms, or an alkoxy group having 1 to 4 carbon atoms; cycloalkyl groups having 3 to 8 carbon atoms which may be substituted by a halogen atom, an alkyl group having 1 to 4 carbon atoms or an alkoxy group having 1 to 4 carbon atoms; and residues of carbohydrates.

Specific examples of the groups of the formula —$COOR^4$ are those in which $R^4$ is the same alkyl group as above having 1 to 10 carbon atoms, or one equivalent of a cation, for example an ammonium cation such as $NH_4^+$, tetramethyl ammonium, monomethyl ammonium, dimethyl ammonium, trimethyl ammonium, benzyl ammonium, phenethyl ammonium, morpholinium cation, monoethanol ammonium or piperidinium cation, an alkali metal cation such as $Na^+$ or $K^+$, or a divalent or trivalent metal cation such as $\frac{1}{2}Ca^{2+}$, $\frac{1}{2}Mg^{2+}$, $\frac{1}{2}Zn^{2+}$ or $\frac{1}{3}Al^{3+}$.

Specific examples of the groups of the formula —$OR^5$ include a hydroxyl group; alkoxy groups having 1 to 6 carbon atoms such as methoxy, ethoxy, n-propoxy, isopropoxy, n-butoxy, n-pentoxy and n-hexoxy; carboacyloxy groups having 1 to 7 carbon atoms such as acetoxy, propionyloxy, n-butyryloxy, isobutyryloxy, n-valeryloxy, isovaleryloxy, caproyloxy, enanthyloxy and benzoyloxy; and a phenoxy group. The $C_{1-6}$ alkoxy groups for —$OR^5$ may be substituted by halogen atoms, thus providing chloromethoxy, dichloromethoxy, trifluoromethoxy, etc. The phenyl moiety of the phenoxy group for —$OR^5$ may be substituted by a halogen atom such as chloro, bromo or fluoro, an alkyl group having 1 to 4 carbon atoms such as methyl, ethyl, propyl or butyl, or an alkoxy group having 1 to 4 carbon atoms such as methoxy, ethoxy, propoxy or butoxy.

A phenyl group or a cycloalkyl group having 3 to 8 carbon atoms may also be substituents for the aforesaid aliphatic hydrocarbon groups. The phenyl group and the $C_{3-8}$ cycloalkyl group may be substituted by the same substituents as described above, i.e. a halogen atom, an alkyl group having 1 to 4 carbon atoms or an alkoxy group having 1 to 4 carbon atoms.

The residue of the carbohydrate may be one of pentose, hexose or heptose, or one of a monosaccharide or polysaccharide. The residue consists of a carbohydrate bearing at least one hydroxyl group binding to the 4,5-disubstituted-2-cyclopentenones. Examples of the carbohydrate include pentose such as ribose, deoxyribose and arabinose; hexose such as glucose and fructose; and heptose such as sodoheptulose.

$R^2$ in formula (I) represents a substituted or -or unsubstituted alkyl, alkenyl or alkynyl group having 1 to 10 carbon atoms. Examples of these groups including substituents on them are the same as given hereinabove. When $R^2$ is an alkenyl group, it is not 2-octenyl, 8-acetoxy-2octenyl or 2,5-octadienyl. These excluded groups are known as the omega-chains of the known natural clavulones or punaglandins. It is complex and troublesome to introduce these groups into the cyclopentanone skeleton by synthesis, and no corresponding advantage is expected.

$R^3$ is a hydrogen atom or a protective group for a hydroxyl group. Examples of the protective group for the hydroxyl group are carboacyl groups, tri($C_{1-7}$ hydrocarbon)silyl groups and groups forming an acetal linkage with the oxygen atom of the hydroxyl group. Specific examples of preferred carboacyl groups include acetyl, propionyl, butyryl, isobutyryl, valeryl, isovaleryl, caproyl, enanthyl and benzoyl.

Specific examples of preferred tri($C_{1-7}$ hydrocarbon)silyl groups include tri($C_{1-4}$ alkyl)silyl groups such as trimethylsilyl, triethylsilyl or t-butyldimethylsilyl, diphenyl($C_{1-4}$ alkyl)silyl groups such as t-butyldiphenylsilyl, and a tribenzylsilyl group.

Examples of the groups forming an acetal linkage together with the oxygen atom of the hydroxyl group include methoxymethyl, 1-ethoxyethyl, 2-methoxy-2-propyl, 2-ethoxy-2-propyl, (2-methoxyethoxy)methyl, benzyloxymethyl, 2-tetrahydropyranyl, 2-tetrahydrofuranyl and 6,6-dimethyl-3-oxa-2-oxo-bicyclo[3.1.0]hex-4-yl groups. Of these, 2-tetrahydropyranyl, 2-tetrahydrofuranyl, 1-ethoxyethyl, 2-methoxy-2-propyl, (2-methoxyethoxy)methyl and 6,6-dimethyl-3-oxa-2-oxo-bicyclo[3.1.0]hex-4-yl groups are particularly preferred.

The compounds of formula (I) may be divided, for convenience, into compounds of formula (I)-a and (I)-b in accordance with the definitions of A and B. Furthermore, according to the definition of $R^1$, they can be divided into a preferred group of 4-hydroxy-2-cyclopentenones of the following formula (I)′

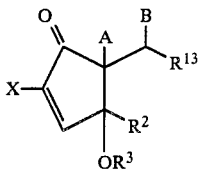

wherein X, A, B, $R^2$ and $R^3$ are as defined above, and $R^{13}$ represents a substituted or unsubstituted alkyl group having 1 to 10 carbon atoms, and a preferred group of 4-hydroxy-2-cyclopentenones represented by the following formula (I)″

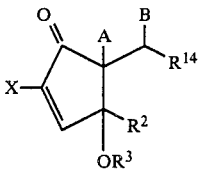

wherein X, A, B, $R^2$ and $R^3$ are as defined above, and $R^{14}$ represents a substituted or unsubstituted $C_2$–$C_{10}$ alken-1-yl group having a carbon-carbon double bond at least at the 1-position. $R^{13}$ in formula (I)′ is, for example, a group of the formula $-CH_2-_5COOR^4$ in which $R^4$ is as defined above.

$R^{14}$ in formula (I)″ is, for example, 3,6-dihydroxy-1-hexen-1-yl or 2,6-dimethyl-1,5-heptadien-1-yl.

In formula (I) including formulae (I)-a, (I)-b, (I)′ and (I)″, the carbon atom at the 4-position of the cyclopentenone ring to which the group $R^2$ and $OR^3$ are bonded is an asymmetric carbon atom. Furthermore, in formula (I) including formulae (I)′ and (I)″ in which A is a hydrogen atom, the carbon atom at the 5-position of the cyclopentenone (the carbon atom to which A is bonded) and the carbon atom at the 5-position of the cyclopentenone ring in formula (I)-b are asymmetric carbon atoms. The compounds of this invention may further have an asymmetric carbon atom, as for example in the case of the carbon atom bonded to the hydroxyl group in formula (I)-b.

The compounds of this invention may have an R- or S-configuration with respect to each of these asymmetric carbon atoms, and may include mixtures of compounds of R- and S-configurations in arbitrary ratios.

Examples of the 4-hydroxy-2-cyclopentenones of formula (I) in accordance with this invention are shown below.

Compounds of formula (I)-a (100) 2-chloro-4-hydroxy-4-octyl-5-[(E)-6-carboxyhexylidene]-2-cyclopentenone,
(102) 2-chloro-4-hydroxy-4-octyl-5-[(Z)-6-carboxyhexylidene]-2-cyclopentenone,
(104) 2-chloro-4-trimethylsilyloxy-4-octyl-5-[(E)-6-carboxyhexylidene]-2-cyclopentenone,
(106) 2-chloro-4-trimethylsilyloxy-4-octyl-5-[(Z)-6-carboxyhexylidene]-2-cyclopentenone,
(108) 2-chloro-4-acetoxy-4-octyl-5-[(E)-6-carboxyhexylidene]-2-cyclopentenone,
(110) 2-chloro-4-acetoxy-4-octyl-5-[(Z)-6-carboxyhexylidene]-2-cyclopentenone,
(112) 2-chloro-4-hydroxy-4-(3,7-dimethyloctyl)-5-[(E)-6-carboxyhexylidene]-2-cyclopentenone,
(114) 2-chloro-4-hydroxy-4-(3,7-dimethyloctyl)-5-[(Z)-6-carboxyhexylidene]-2-cyclopentenone,
(116) 2-chloro-4-trimethylsilyloxy-4-(3,7-dimethyloctyl)-5-[(E)-6-carboxyhexylidene]-2-cyclopentenone,
(118) 2-chloro-4-trimethylsilyloxy-4-(3,7-dimethyloctyl)-5-[(Z)-6-carboxyhexylidene]-2-cyclopentenone,
(120) 2-chloro-4-acetoxy-4-(3,7-dimethyloctyl)-5-[(E)-6-carboxyhexylidene]-2-cyclopentenone,
(122) 2-chloro-4-acetoxy-4-(3,7-dimethyloctyl)-5-[(Z)-6-carboxyhexylidene]-2-cyclopentenone,
(124) 2-chloro-4-hydroxy-4-[3-(3,4-dimethoxyphenyl)propyl]-5-[(E)-6-carboxyhexylidene]-2-cyclopentenone,
(126) 2-chloro-4-hydroxy-4-[3-(3,4-dimethoxyphenyl)propyl]-5-[(Z)-6-carboxyhexylidene]-2-cyclopentenone,
(128) 2-chloro-4-trimethylsilyloxy-4-[3-(3,4-dimethoxyphenyl)propyl]-5-[(E)-6-carboxyhexylidene]-2-cyclopentenone,
(130) 2-chloro-4-trimethylsilyloxy-4-[3-(3,4-dimethoxyphenyl)propyl]-5-[(Z)-6-carboxyhexylidene]-2-cyclopentenone,
(132) 2-chloro-4-acetoxy-4-[3-(3,4-dimethoxyphenyl)propyl]-5-[(E)-6-carboxyhexylidene]-2-cyclopentenone,
(134) 2-chloro-4-acetoxy-4-[3-(3,4-dimethoxyphenyl)propyl]-5-[(Z)-6-carboxyhexylidene]-2-cyclopentenone,
(136) 2-chloro-4-(4-phenoxybutyl)-4-hydroxy-5-(3,7-dimethyl-2,6-octadienylidene)-2-cyclopentenone,
(138) 4-butyl-5-[(E)-butylidene]-4-hydroxy-2-cyclopentenone,
(140) 4-butyl-5-[(Z)-butylidene]-4-hydroxy-2-cyclopentenone,
(142) (4R)-5-[(E)-6-methoxycarbonylhexylidene]-4-hydroxy-4-octyl-2-cyclopentenone,
(144) (4R)-5-[(Z)-6-methoxycarbonylhexylidene]-4-hydroxy-4-octyl-2-cyclopentenone,
(146) 5-[(E)-4,7-dihydroxy-(2E)-pentenylidene]-4-(4-phenoxybutyl)-4-hydroxy-2-cyclopentenone,
(148) 5-[(Z)-4,7-dihydroxy-(2E)-pentenylidene]-4-(4-phenoxybutyl)-4-hydroxy-2-cyclopentenone,
(150) 4-(4-phenoxybutyl)-4-hydroxy-5-(3,7-dimethyl-2,6-octadienylidene)-2-cyclopentenone),
(152) 2-chloro-4-hydroxy-4-[3-(3,4-dimethoxyphenyl)propyl]-5-(6-methoxycarbonylhexylidene)-2-cyclopentenone,
(154) 2-chloro-4-hydroxy-5-(6-methoxycarbonylhexylidene)-4-octyl-2-cyclopentenone, (156) 2-chloro-4-(3,7-dimethyloctyl)-4-hydroxy-5-[(Z)-6-methoxycarbonylhexylidene]-2-cyclopentenone, (158) 2-chloro-4-(3,7-dimethyloctyl)-4-hydroxy-5-[(E)-6-methoxycarbonylhexylidene]-2-cyclopentenone.

Compounds of formula (I)-b (200) 2-chloro-4-hydroxy-4-octyl-5-(1-hydroxy-6carboxyhexyl)-2-cyclopentenone, (202) 2-chloro-4-trimethylsilyloxy-4-octyl-5-(1-hydroxy-6-carboxyhexyl)-2-cyclopentenone, (204) 2-chloro-4-acetoxy-4-octyl-5-(1-hydroxy-6-carbohexyl)-2-cyclopentenone, (206) 2-chloro-4-hydroxy-4-(3,7-dimethylocyl)-5-(1-hydroxy-6-carboxyhexyl)-2-cyclopentenone, (208) 2-chloro-4-trimethylsilyloxy-4-(3,7-dimethyloctyl)-5-(1-hydroxy-6-carboxyhexyl)-2-cyclopentenone, (210) 2-chloro-4-acetoxy-4-(3,7-dimethyloctyl)-5-(1-hydroxy-6-carboxyhexyl)-2-cyclopentenone, (212) 2-chloro-4-hydroxy-4-[3-(3,4-dimethoxyphenyl)-propyl]-5-(1-hydroxy-6-carboxyhexyl)-2-cyclopentenone, (214) 2-chloro-4-trimethylsilyloxy-4-[3-(3,4dimethoxyphenylpropyl]-5-(1-hydroxy-6-carboxyhexyl)-2-cyclopentenone, (216) 2-chloro-4-acetoxy-4-[3-(3,4-dimethoxyphenyl)-propyl]-5-(1-hydroxy-6-carboxyhexyl)-2-cyclopentenone, (218) 4-butyl-5-(1-hydroxybutyl)-4-trimethylsilyloxy-2-cyclopentenone, (220) 4-trimethylsilyloxy-5-(1-hydroxy-6-methoxycarbonylhexyl)-4-octyl-2-cyclopentenone, (222) 5-(4,7-di-t-butyldimethylsilyloxy-1-hydroxy-2-hepten-1-yl)-4-(4-phenoxybutyl)-4-trimethylsilyloxy--2-cyclopentenone, (224) 4-(4-phenoxybutyl)-4-trimethylsilyloxy-5-(3,7-dimethyl-1-hydroxy-2,6-octadiene)-2-cyclopentenone, (226) 2-chloro-4-hydroxy-4-[3-(3,4-dimethoxyphenyl)-propyl]-5-(1-hydroxy-6-methoxycarbonylhexyl)-2-cyclopentenone, (228) 4-(4-phenoxybutyl)-4-hydroxy-5-(3,7-dimethyl-1-hydroxy-2,6-octadiene)-2-cyclopentenone.

The 4-hydroxy-2-cyclopentenones of formula (I)-b of this invention can be produced in accordance with this invention by subjecting a compound represented by the following formula (II)-b

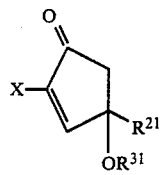

(II)-b wherein X represents a hydrogen or halogen atom, $R^{21}$ represents as substituted or unsubstituted alkyl, alkenyl or alkynyl group having 1 to 10 carbon atoms, and $R^{31}$ represents a protective group for a hydroxyl group, provided that $R^{21}$ is not 2-octenyl, 8-acetoxy-2-octenyl or 2,5-octadienyl, and an aldehyde reepresented by the following formula (III)

(III)

wherein $R^{11}$ represents a substituted or unsubstituted alkyl, alkenyl or alkynyl group having 1 to 10 carbon atoms, to aldol condensation, and if required, subjecting the resulting product to deprotection, hydrolysis and-/or salt-forming reaction.

The starting compound of formula (II)-b is a novel compound. X is a hydrogen or halogen atom. $R^{21}$ represents a substituted or unsubstituted alkyl, alkenyl or alkynyl group having 1 to 10 carbon atoms. $R^{31}$ is a protective group for a hydroxyl group. Specific examples of X are as given hereinabove, and specific examples of $R^{21}$ and $R^{31}$ are the same as those given above for $R^2$ and $R^3$ with regard to formula (I).

On the other hand, in the other starting compound of formula (III), $R^{11}$ represents a substituted or unsubstituted alkyl, alkenyl or alkynyl group having 1 to 10 carbon atoms. Specific examples of these are the same as those given above for $R^1$ with regard to formula (I).

In the process of this invention, the compound of formula (II)-b and the compound of formula (III) are first subjected to aldol condensation. The aldol condensation reaction is carried out in a solvent in the presence of a basic compound. Compounds suitably used as the basic compound and the reaction solvent are, for example, those described in A. T. Nielsen, W. J. Houlihan: Org. React., 16, 1 (1968); H. O. House, "Modern Synthetic Reactions", 2nd edition, Benjamin (1972), p. 629; and Shin Jikken Kagaku Koza, 14, II 736, III 851.

In the aldol condensation reaction, a dialkylboron trifluoromethanesulfonic acid such as dibutylboron trifluoromethanesulfonic acid is used in the presence of a metal amide such as lithium diisopropyl amide, lithium diethyl amide or lithium bistrimethylsilyl amide or a tertiary amine such as triethylamine, diisopropylethylamine or triethylbutylamine.

When the aldol condensation reaction is carried out by using the metal amide, the amount of the metal amide is, for example, 0.3 to 30 equivalents, preferably 0.9 to 10 equivalents, relative to the compound of formula (II)-b. Examples of the reaction solvent are ethers such as diethyl ether or tetrahydrofuran, and hydrocarbons such as petroleum ether, hexane and pentane. The reaction temperature is preferably −100° to 50° C., especially preferably −80° to 0° C.

When the aldol condensation reaction is carried out in the presence of the tertiary amine using the dikylboron trifluoromethanesulfonic acid, the amount of each of these compounds used is, for example, 0.5 to 50 equivalents, preferably 1 to 10 equivalents, relative to the compound of formula (II)-b.

The amount of the aldehyde of formula (III) as the other starting material is, for example, 0.5 to 10 equivalents, preferably 0.8 to 2 equivalents, relative to the compound of formula (II)-b.

The reaction time varies depending upon the types of the starting compounds, the reagents, the reaction solvent used. Usually, it is 5 minutes to 24 hours, preferably 10 minute to 12 hours.

After the reaction, the product can be purified and recovered by usual means such as extraction, washing with water, drying and chromatography. As required, the product may be subjected to deprotection, hydrolysis, or salt-forming reaction.

Elimination of the hydroxyl-protective group can be carried out as follows.

When the protective group forms an acetal linkage together with the oxygen atom of the hydroxyl group, the deprotection reaction is carried out, for example, by using acetic acid, a pyridinium salt of p-toluenesulfonic acid or a cation exchange resin as a catalyst and water, tetrahydrofuran, ethyl ether, dioxane, acetone or acetonitrile as a solvent. The reaction is carried out usually at a temperature of $-78°$ to $+30°$ C. for a period of about 10 minutes to about 3 days.

When the protective group is a tri($C_1$-$C_7$)hydrocarbon-silyl group, the deprotection reaction is carried out at the same temperature as above in the above-exemplified reaction solvent in the presence of acetic acid, tetrabutyl ammonium fluoride, cesium fluoride, etc.

When the protective group is an acyl group, it can be split off by hydrolysis in, for example, an aqueous solution of sodium hydroxide, potassium hydroxide or calcium hydroxide, a water-alcohol mixture, or a methanol or ethanol solution containing sodium methoxide, potassium methoxide or sodium ethoxide.

When the final compound has an ester group, it may be hydrolyzed. Hydrolysis may be carried out by using an enzyme such as lipase in water or an aqueous solution at a temperature of $-10°$ C. to $+60°$ C. for a period of about 10 minutes to 24 hours.

Where the final compound has a carboxyl group in the molecule, it may, if required, be subjected to a salt-forming reaction to obtain the corresponding carboxylate. The salt-forming reaction is known per se. It may be carried out, for example, by reacting it with a basic compound such as sodium hydroxide, potassium hydroxide or sodium carbonate, ammonia, trimethylamine, monoethanolamine or morpholine in an amount nearly equal to that of the carboxylic acid for neutralization.

Thus, the above process of this invention can give 4-hydroxy-2-cyclopentenones of the following formula (I)-b

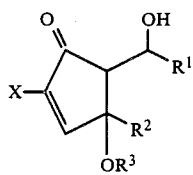

wherein X, $R^1$, $R^2$ and $R^3$ are as defined.

The compound of formula (II)-b used as a starting material in the above reaction can be produced by reacting a 4-hydroxy-2-cyclopenten-1-one of the following formula (A), which is known per se. (W. Richards, et al., J. C. S. Chemical Communication, 121, 1979),

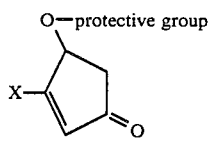

with MgBr$R^2$ or Li$R^2$ by a method known per se to form a 3,5-dihydroxycyclopent-1-ene of the following formula (B)

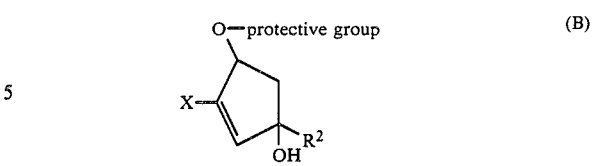

splitting off the protective group from the resultant compound, selectively oxidizing it (E. J. Corey et al., J. A. C. S., 106 3384, 1984; Y. Yamada et al., Tetrahedron Leters., 25 3621, 1984) to form a compound of the following formula (C)

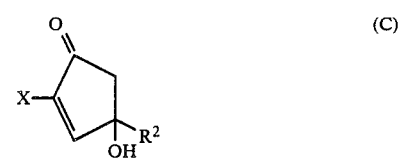

and protecting the hydroxyl group of the resultant compound. Compounds represented by the following formula (IV)

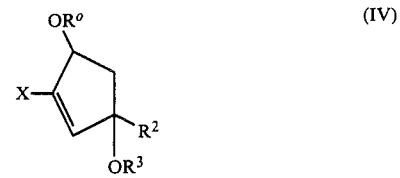

wherein X, $R^2$ and $R^3$ are as defined hereinabove and $R^o$ represents a hydrogen atom or a protective group for a hydroxyl group, which embraces the compounds of formula (B) above and also compounds easily derived from these compounds constitute a group of novel compounds provided by this invention.

Compounds represented by the following formula (II) which embrace the compounds represented by formulae (C) and (II)-b above

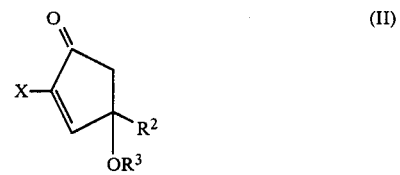

wherein X, $R^2$ and $R^3$ are as defined above, also constitute a group of novel compounds provided for the first time by the present invention.

Specific examples of the compounds represented by formula (IV) [including formula (B)] and formula (II) [including formulae (C) and (II)-b] will be self-evident from the specific examples of X, $R^2$ and $R^3$ given hereinabove with regard to formula (I). Specific examples of the protective group represented by $R^o$ are the same as those given for $R^3$.

The 4-hydroxy-2-cyclopentenones of formula (I)-a can be produced in accordance with this invention by subjecting a compound represented by the following formula (I)-b'

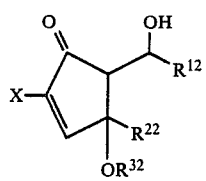

(I)-b' wherein X is as defined above, $R^{12}$ represents a substituted or unsubstituted alkyl, alkenyl or alkynyl group having 1 to 10 carbon atoms, $R^{22}$ represents a substituted or unsubstituted alkyl, alkenyl or alkynyl group having 1 to 10 carbon atoms, and $R^{32}$ represents a protective group for a hydroxyl group, provided that $R^{22}$ is not 2-octenyl, 8-acetoxy-2-octenyl or 2,5-octadienyl, and as required, subjecting the resulting compound to deprotection, hydrolysis and/or salt-forming reaction.

In formula (I)-b', X is as defined hereinabove, and $R^{12}$ and $R^{22}$, independently for each other, represent a substituted or unsubstituted $C_1$–$C_{10}$ C alkyl, alkenyl or alkynyl group. Specific examples of $R^{12}$ and $R^{22}$ may be the same as those of $R^1$ and $R^2$ given hereinabove. The protective group for a hydroxyl group represented by $R^{32}$ may be the same as the protective group represented by $R^3$ given hereinabove.

According to the process of this invention, the compound of formula (I)-b' is subjected to dehydration reaction. The dehydration reaction is carried out preferably by using a basic compound and a reactive derivative of an organic sulfonic acid. Specifically, it is preferred to treat the compound of formula (I)-b' first with the basic compound and the reactive derivative of an organic sulfonic acid, and then treating the product further with the basic compound. First, the hydroxyl group of the compound of formula (I)-b' is sulfonylated, and then split off as an organic sulfonic acid, whereupon the dehydration reaction is completed.

Amines are preferred as the basic compound used together with the derivative of an organic sulfonic acid. Examples of the amines include pyridine, 4-dimethylaminopyridine, triethylamine, diisopropylcyclohexylamine, 1,5-diazabicyclo[4.3.0]non-5-ene (DBN for short), 1,8-diazabicyclo[5.4.0]undec-7-ene (DBU for short), quinacridine, triethylenediamine, isopropyldimethylamine and diisopropylethylamine. Of these, pyridine, 4-dimethylaminopyridine, DBU and DBN are preferred.

Examples of the reactive derivative of organic sulfonic acid include organic sulfonic acid halides such as methanesulfonyl chloride, ethanesulfonyl chloride, n-butanesulfonyl chloride, t-butanesulfonyl chloride, trifluoromethanesulfonyl chloride, benzenesulfonyl chloride and p-toluenesulfonyl chloride; and organic sulfonic acid anhydrides such as methanesulfonic anhydride, ethanesulfonic anhydride, trifluoromethanesulfonic anhydride, benzenesulfonic anhydride and p-toluenesulfonic anhydride.

The above basic compounds themselves may be used as a solvent for the reaction. Other examples of the solvent include halogenated hydrocarbons such as dichloromethane, chloroform, carbon tetrachloride and dichloroethane; ethers such as diethyl ether and tetrahydrofuran; and hydrocarbons such as benzene, toluene, pentane, hexane and cyclohexane. Pyridine and dichloromethane are preferred.

The amount of the derivative of an organic sulfonic acid is preferably 1 to 10 equivalents per mole of the compound of general formula (I)-b'.

The amount of the basic compound is at least 1 equivalent, preferably at least 2 equivalents, relative to the above reactive derivative of an organic sulfonic acid.

The amount of the sovlent used is usually 1 to 1000 times, preferably 5 to 100 times, the volume of the compound of formula (I)-b'.

The reaction temperature varies depending upon the starting compound, the basic compound, solvent, etc., and is usually −10° C. to 50° C., preferably 0° to 30° C. The reaction time varies over a wide range depending upon various conditions, and is about 0.1 to 10 hours. The progress of the reaction can be monitored, for example, by thin-layer chromatography.

Thus, as a result of the above reaction (to be referred to as the first reaction), an organic sulfonyloxy derivative of the cyclopentenone of formula (I)-b' is formed by the conversion of the hydroxyl group on the 5-position alkyl group into an organic sulfonyloxy group. The resulting compound is then reacted with the basic compound (to be referred to as the second reaction) to split off the corresponding organic sulfonic acid and thus converted to a 4-hydroxy-2-cyclopentenone represented by the following formula (I)-a'

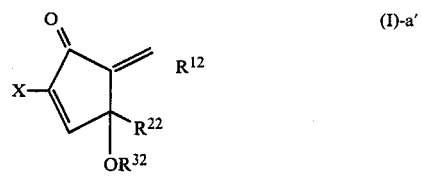

(I)-a' wherein X, $R^{12}$ and $R^{32}$ are as defined above.

Examples of the basic compound that can be used in the second reaction may be the same as those given hereinabove with regard to the basic compound used in the first reaction. The basic compound used in the second reaction may be different from that used in the first reaction.

The second reaction can be carried out at the same temperature. The organic sulfonyloxy derivative formed in the first reaction may be subjected to the second reaction after isolating it or in the same reaction system as in the first reaction. After the reaction, the desired compound is purified and recovered by usual means.

As required, the resulting 4-hydroxy-2-cyclopentenone may be subjected to deprotection, hydrolysis, and/or salt-forming reaction as stated above.

As a result, the process of this invention can give the compounds of formula (I)-a.

The 4-hydroxy-2-cyclopentenones of this invention show an especially strong effect of suppressing the proliferation of L1210 leukemia cells even when used in low concentrations. This is ample evidence that the compounds of this invention are useful as antitumor drugs.

The compounds of this invention can be administered orally, or parenterally through, for example, percutaneous, subcutaneous, intramuscular, intravenous, intraarterial and intrarectal routes.

Preparations for oral administration may be in the form of, for example, tablets, pills, granules, powders, solutions, suspensions and capsules.

Tablets may be formulated in a usual manner by using excipients such as lactose, starch, calcium carbonate, crystalline cellulose and silicic acid, binders such as carboxymethyl cellulose, methyl cellulose, potassium phosphate and polyvinyl pyrrolidone, disintegrants such as sodium alginate, sodium hydrogen carbonate, sodium lauryl sulfate and stearyl monoglyceride, moisturizers such as glycerin, absorbents such as kaolin and colloidal silica and lubricants such as refined talc and powdered boric acid. Pills, powders and granules can also be formulated by ordinary methods using the excipients and other carriers mentioned above.

Solutions and suspensions may be formulated by ordinary methods using glycerol esters such as tricaprylin and triacetin, purified water, and alcohols such as ethanol.

Capsules may be formulated by filling the granules, powders or solutions prepared as above into gelatin capsules.

Preparations for percutaneous administration may be in the form of, for example, ointments and creams. Ointments may be formulated in a customary manner using fatty oils such as castor oil, olive oil and vaseline. Creams may be formulated in a customary manenr using fatty oils and emulsifying agents such as diethylene glycol and sorbitan fatty acid monoesters.

Injectable preparations formulated in solutions or suspensions may be used for subcutaneous, intramuscular, intraveous or intraarterial administration. In the preparation of solutions and suspensions, propylene glycol, polyethylene glycol, olive oil, ethyl oleate, ester of iodinated pappy seed oil, etc. may generally be used, and as requried, a small amount of an antiseptic, stabilizer, etc. may be added. The injectable preparations can be sterilized by filtration through a bacterial filter and by addition of a bactericide.

The injectable preparations may be used in the form of lipid microspheres.

Ordinary suppositories formulated by using soft gelatin capsules are used for intrarectal administration.

The 4-hydroxy-2-cyclopentenones as the active ingredients of such pharmaceutical preparations can also be included as inclusion compounds formed with alpha-, beta- and gamma-cyclic dextrins or their methylated cyclic dextrins.

The effective dose of the compounds of this invention varies with the age, sex, condition, etc. of a patient to be treated. It is usually in the range of $10^2$ to $2 \times 10^5$ micrograms/kg/day, preferably in the range of $5 \times 10^2$ to $10^4$ micrograms/kg/day.

As described above in detail, the present invention provides the novel 4-hydroxy-2-cyclopentenones which are useful as antitumor drugs either by themselves or as antitumor preparations containing them as active ingredients.

The following examples are given to illustrate the present invention in more detail.

EXAMPLE 1

Production of
2-chloro-5-(1-hydroxy-6-methoxycarbonylhexyl)-4-octyl-4-trimethylsilyloxy-2-cyclopentenone (1) Production of
2-chloro-4-octylcyclopent-2-ene-1,4-diol 108 mg of 3-chloro-4-t-butyldimethylsilyloxy-2-cyclopentenone was dissolved in 4 ml of ether, and the solution was cooled to −78° C. Then, 0.79 ml of a 0.72 M tetrahydrofuran solution of octyl magnesium bromide was added. The mixture was stirred for 10 minutes, and water was added. The mixture was extracted with ether, and the extract was dried over anhydrous magnesium sulfate, filtered, and concentrated. The resulting oily product was dissolved in 6 ml of tetrahydrofuran, and 1.1 ml of a 1 M tetrahydrofuran solution of tetrabutyl ammonium fluoride was added. The mixture was stirred for 2 days. A saturated aqueous solution of sodium chloride was added, and the mixture was extracted with ethyl acetate. The extract was dried over anhydrous sodium sulfate, filtered, and concentrated. The concentrate was chromatographed on a silica gel column to give 92 mg (yield 83%) of 2-chloro-4-octyl-cyclopent-2-ene-1,4-diol.

(2) Production of
2-chloro-4-hydroxy-4-octyl-2-cyclopentenone 700 mg of 2-chloro-4-octylcyclopent-2-ene-1,4-diol obtained in accordance with (1) was dissolved in 8 ml of diemthylformamide, and 1.68 g of pyridinium dichromate was added. The mixture was stirred for 20 hours. After filtration, a saturated aqueous solution of sodium chloride was added, and the mixture was extracted with ether. The extract was dried over anhydrous magnesium sulfate, filtered, and concentrated. The concentrate was chromatographed on a silica gel column to give 547 mg (yield 75%) of 2-chloro-4-hydroxy-4-octyl-2-cyclopentenone. The NMR spectral data of the product were as follows:

NMR ($\delta$ ppm, CDCl$_3$):
0.7–1.0 (3H, br, t), 1.1–2.0 (15H, m),
2.53 (1H, d, J=18.7 Hz), 2.77 (1H, d, J=18.7 Hz),
7.33 (1H, s). (3) Production of 2-chloro-4-octyl-4-trimethylsilyloxy-2-cyclopentenone
77 mg of 2-chloro-4-hydroxy-4-octyl-2-cyclopentenone obtained in accordance with (2) was dissolved in 4 ml of dichloromethane, and 0.54 ml of diisopropylethylamine was added. Furthermore, 0.07 ml of trimethylsilyltrifluoromethanesulfonic acid was added, and the mixture was stirred for 15 minutes. Water was added, and the mixture was extracted with dichloromethane. The organic layer was dried over anhydrous sodium sulfate, filtered, and concentrated. The concentrate was chromatographed on a silica gel column to give 96 ml (yield 97%) of 2-chloro-4-octyl-4-trimethylsilyloxy-2-cyclopentenone.

NMR ($\delta$ 6 ppm, CDCl$_3$):
0.08 (9H, s), 0.7–1.0 (3H, br, t), 1.1–1.9
(14H, m), 2.63 (2H, s), 7.34 (1H, s).

(4) Production of
2-chloro-5-(1-hydroxy-6-methoxycarbonylhexyl)-4-octyl-4-trimethylsilyloxy-2-cyclopentenone 526 mg of 2-chloro-4-octyl-4-trimethylsilyloxy-2-cyclopentenone obtained in accordance with (3) above was dissolved in 18 ml of ether. The solution was cooled to −78° C., and 2.03 ml of a 1.0 M dichloromethane solution of dibutylboron and trifluoromethanesulfonic acid was added, and the mixture was stirred for 30 minutes. A solution of 321 mg of methyl 7-oxoheptanoate in 7 ml of ether was added. The mixture was stirred at −78° C. for 80 minutes, and an aqueous solution of ammonium chloride was added. The mixture was extracted with ether. The extract was dried over anhydrous magnesium sulfate, filtered, and concentrated. The concentrate was chromatographed on a silica gel column to give 360 mg (yield 46%) of a mixture of isomers of 2-chloro-5-(1-hydroxy-6-methoxycarbonyhexyl)-4-octyl-4-trimethylsilyloxy-2-cyclopentenone.

NMR (δ ppm, CDCl₃):
0.13 and 0.19 (9H, s), 0.7–1.0 (3H, br, t),
1.0–2.0 (23H, m), 2.32 (2H, t, J=7.2 Hz),
2.42 (1H, d), 3.66 (3H, s), 3.8–4.1 (1H, m),
7.32 and 7.47 (1H, s).

EXAMPLE 2

Production of 2-chloro-5-(6-methoxycarbonylhexylidene)-4-octyl-4-trimethylsilyloxy-2-cyclopentenone 171 mg of 2-chloro-5-(1-hydroxy-6-methoxy-2cyclopentenone obtained in Example 1 was dissolved in 7 ml of pyridine, and 50 microliters of methanesulfonyl chloride was added. The mixture was stirred for 14 hours. Water was added, and the mixture was extracted with dichloromethane. The extract was dried over anhydrous sodium sulfate, filtered and concentrated. The resulting oily product containing 2-chloro-5-(1-methanesulfonyloxy-6-methoxycarbonylhexyl)-4-octyl-4-trimethylsilyloxy-2-cyclopentenone was dissolved in 10 ml of benzene, and 0.1 ml of 1,8-diazabicyclo[5.4.0]undec-7-ene was added, and the mixture was stirred for 55 minutes. Water was added, and the mixture was extracted with ether. The extract was dried over anhydrous magnesium sulfate, filtered and concentrated. The concentrate was chromatographed on a silica gel column to give 73 mg (yield 43%) of a mixture of Z- and E-isomers of 2-chloro-5-(6-methoxycarbonylhexylidene)-4-octyl-4-trimethylsilyloxy-2-cyclopentenone.

NMR (δ ppm, CDCl₃):
0.03 (9H, s), 0.7–1.0 (3H, br, t), 1.0–2.0
(20H, m), 2.1–2.5 (4H, m), 3.68 (3H, s),
6.66 (1H, t, J=7.7 Hz), 7.20 (1H, s).

EXAMPLE 3

Production of 2-chloro-4-hydroxy-5-(6-methoxycarbonylhexylidene)-4-octyl-2-cyclopentenone 31 g of the mixture of E- and Z-isomes of 2-chloro-5-(6-methoxycarbonylhexylidene)-4-octyl-4-trimethylsilyloxy-2-cyclopentenone obtained in Example 2 was mixed with 3 ml of a 6:1:3 mixture of acetic acid, tetrahydrofuran and water, and the mixture was stirred for 2 hours. A saturated aqueous solution of sodium bicarbonate was added, and the mixture was extracted with ether. The extract was dried over anhydrous sodium sulfate, filtered, and concentrated. The concentrate was chromatographed on a silica gel column to give 25 mg (yield 97%) of a mixture of Z- and E-isomers of 2-chloro-4-hydroxy-5-(6-methoxxycarbonylhexylidene-4-octyl-2-cyclopentenone.

NMR (δ ppm, CDCl₃):
0.7–1.1 (3H, t), 1.1–2.1 (21H, m), 2.35 (2H, t),
2.5–3.0 (2H, m), 3.67 (3H, s), 6.35 (1WlH, t, J=7.9 Hz), 6.66 (1H, dd, J=8.3 and 7.5 Hz), 7.17 (1H, s), 7.24 (1H, s).

EXAMPLE 4

Production of 2-chloro-4-(3,7-dimethyloctyl)-5-(1-hydroxy-6-methoxycarbonylhexyl)-4-trimethylsilyloxy-2-cyclopentenone (1) Production of 3-t-butyldimethylsilyloxy-2-chloro-5-(3,7-dimethyloctyl)-5-hydroxycyclopentene The procedure of Example 1, (1) was repeated using 3.70 g of 4-t-butyldimethylsilyloxy-3-chloro-2-cyclopentenone and an ether solution of 3,7-dimethyloctyl magnesium bromide. There were obtained 3.17 g of a low polarity isomer of 3-t-butyldimethylsilyloxy-2-chloro-5-(3,7-dimethyloctyl)-5-hydroxycyclopentene, 0.60 g of a high polarity isomer of it, and 1.12 g of a mixture of these isomers (yield 84%).

The spectral data were as follows:

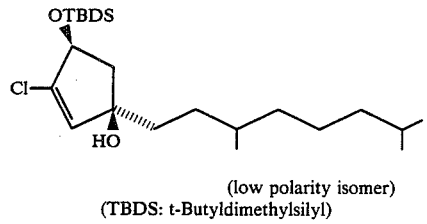

(low polarity isomer)
(TBDS: t-Butyldimethylsilyl)

NMR (δ ppm, CDCl₃):
0.13 (6H, s), 0.7–1.0 (9H, m), 0.87 (9H, s),
1.0–1.8 (12H, m), 1.78 (1H, dd, J=14.0 and 3.0 Hz),
2.15 (1H, s), 2.36 (1H, dd, J=14.0 and 6.4 Hz), 4.38 (1H, dd, J=6.2 and 3.8 Hz),
5.71 (1H, s).

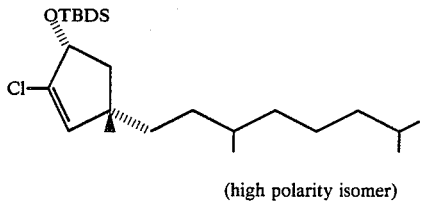

(high polarity isomer)

NMR (δ ppm, CDCl₃)
0.1–0.3 (6H, m), 0.7–1.0 (9H, m), 0.87 (9H, s),
1.0–1.8 (12 H, m), 1.68 (1H, s), 1.84 (1H, dd, J=12.4 and 4.2 Hz), 2.19 (1H, dd, J=12.4 and 6.4 Hz), 4.6–4.9 (1H, m), 5.63 (1H, s).

(2) Production of 2-chloro-4-(3,7-dimerthyloctyl)-4-hydroxy-2-cyclopentenone 50 mg of 3-t-butyldimethylsilyloxy-2-chloro-5-(3,7-dimethyloctyl)-5-hydroxycyclopentene obtained in (1) above was dissolved in 1 ml of tetrahydrofuran, and 200 mg of tetrabutyl ammonium fluoride trihydrate was added. The mixture was stirred for 4 hours. A saturated aqueous solution of ammonium chloride was added, and the mixture was extracted with ethyl acetate. The organic layer was washed with an aqueous solution of sodium chloride, and dried over anhydrous magnesium sulfate. After filtration and concentration, 30 mg of a crude product of 1-chloro-3(3,7-dimethyloctyl)-3,5-dihydroxycyclopentene was obtained. The crude product was dissolved in 1 ml of dimethylformamide, and 100 mg of pyridinium dichromate was added. The mixture was stirred for 2 hours. Water was added, and the mixture was extracted with ethyl acetate. The organic layer was washed with an aqeuous solution of sodium chloride, and dried over anhydrous magnesium sulfate. After filtration and concentration, the residue was chromatographed on a silica gel column to give 14 mg (yield 40%) of 2-chloro-4-(3,7-dimethyloctyl)-4-hydroxy-2-cyclopentenone.

NMR (δppm, CDCl$_3$): 0.7–1.0 (9H, m), 1.0–2.4 (12H, m), 2.56 (1H, s), 7.33 (1H, s).

(3) Production of 2-chloro-4-(3,7-dimethyloctyl-4-trimethylsilyloxy-2-cyclopentenone)

To 147 mg of 2-chloro-4-(3,7-dimethyloctyl)-4hydroxy-2-cyclopentenone obtained in accordance with (2) above was added 700 microliters (2.6 mmoles) of N,O-bistrimethylsilyl trifluoroacetamide, and the mixture was stirred for 16 hours. The reaction mixture was chromatographed on a silica gel column to give 165 mg (yield 89%) of 2-chloro-4-(3,7-dimethyloctyl)-4-trimethylsilyloxy-2-cyclopentenone.

NMR (δppm, CDCl$_3$): 0–0.3 (9H, m), 0.7–1.0 (9H, m), 1.0–2.0 (12H, m), 2.57 (2H, s), 7.30 (1H, s).

(4) Production of 2-chloro-4-(3,7-dimethyloctyl)-5-(1-hydroxy-6-methoxycarbonylhexyl)-4-trimethylsilyloxy-2-cyclopentenone 54 mg (157 micromoles) of 2-chloro-4-(3,7-dimethyloctyl)-4-trimethylsilyloxy-2-cyclopentenone obtained in (3) above was dissolved in 2 ml of tetrahydrofuran. The solution was cooled to −45° C., and 1.5 ml (0.30 mmole) of a 0.2 M tetrahydrofuran solution of lithium diisopropylamide was added. The solution was stirred at −45° C. for 20 minutes. 47 mg (0.3 mmole) of methyl 7-oxoheptanoate was dissolved in 1 ml of dry tetrahydrofuran. The solution was cooled to −45° C., and added to the above reaction mixture. The mixture was stirred at −45° C. for 20 minutes. Acetic acid (100 microlitters) was added, and the mixture was stirred for 5 minutes. The reaction mixture was poured onto a saturated aqueous solution of ammonium chloride, and extracted with ethyl acetate. The organic layer was washed with a saturated aqueous solution of sodium chloride, and washed with anhydrous magnesium sulfate. After filtration and concentration, the residue was chromnatographed on a silica gel column to recover 24 mg of the starting material and give 22 mg (yield 50%) of 2-chloro-4-(3,7-dimethyloctyl)-5-(1-hydroxy-6-methoxycarbonylhexyl)-4-trimethylsilyloxy-2-cyclopentenone.

NMR (δppm, CDCl$_3$): 0.20 (9H, s), 0.7–1.0 (9H, m), 1.0–2.0 (20H, m), 2.0–2.7 (3H, m), 2.9–3.5 (1H, m), 3.60 (3H, s), 3.5–4.2 (1H, m), 7.25–7.4 (1H, m).

EXAMPLE 5

Production of 2-chloro-4-(3,7-dimethyloctyl)-5-[(Z)-6-methoxycarbonylhexylidene]-4-trimethylsilyloxy-2-cyclopentenone and 2-chloro-4-(3,7-dimethyloctyl)-5-[(E)-6-methoxycarbonylhexylidene]-4-trimethylsilyloxy-2-cyclopentenone 22 mg (44 micromoles) of 2-chloro-4-(3,7-dimethyloctyl)-5-(1-hydroxy-6-methoxycarbonyl)-4-trimethylsilyloxy-2-cyclopentenone obtained in Example 4 was dissolved in 500 microliters of pyridine, and 50 microliters (646 micromoles) of methanesulfonyl chloride was added. The mixture was stirred for 1.5 hours. 200 microliters (1.34 mmoles) of 1,8-diazabicyclo[5.4.0]undec-7-ene was added, and the mixture was stirred for 30 minutes. A saturated aqueous solution of potassium hydrogen sulfate was added, and the mixture was extracted with ethyl acetate. The organic layers were combined, washed successively with a saturated aqueous solution of sodium hydrogen carbonate and a saturated aqueous solution of sodium chloride, and dried over anhydrous sodium sulfate. After filtration and concentration, the residue was chromatographed on a thin silica gel layer to give 6.3 mg (yield 30%) of 2-chloro-4-(3,7-dimethyloctyl)-5-[(Z)-6-methoxycarbonylhexylidene]-4-trimethylsilyloxy-2-cyclopentenone and 11.0 mg (yield 52%) of 2-chloro-4-(3,7-dimethyloctyl)-5-[(E)-6-methoxycarbonylhexylidene]-4-trimethylsilyloxy-2-cyclopentenone.

Spectral data of the Z-isomer:

NMR (δppm, CDCl$_3$): 0–0.3 (9H, m), 0.7–1.0 (9H, m), 1.0–2.0 (18H, m), 2.0–2.5 (2H, m), 2.5–3.0 (2H, m), 3.61 (3H, s), 6.21 (1H, t, J=7.5 Hz), 7.07 (1H, s).

Spectral data of the E-isomer:

NMR (δppm, CDCl$_3$): 0–0.3 (9H, m), 0.7–1.0 (9H, m), 1.0–2.0 (18H, m), 2.0–2.8 (4H, m), 3.63 (3H, s), 6.63 (1H, t, J=7.5 Hz), 7.17 (1H, s).

EXAMPLE 6

Production of 2-chloro-4-(3,7-dimethyloctyl)-4-hydroxy-5-[(Z)-6-methoxycarbonylhexylidene]-2-cyclopentenone 6.3 mg (13 micromoles) of 2-chloro-4-(3,7-dimethyloctyl)-5-[(Z)-methoxycarbonylhexylidene]-4-trimethylsilyloxy-2-cyclopentenone obtained in accordance with Example 5 was dissolved in 0.5 ml of a 3:1:1 mixture of acetic acid, tetrahydrofuran and water. A saturated aqueous solution of sodium hydrogen carbonate was added, and the mixture was extracted with ethyl acetate. The organic layer was washed with a saturated aqueous solution of sodium chloride, and dried over anhydrous sodium sulfate. After filtration and concentration, the residue was chromatographed on a thin silica gel column to give 5.2 mg (yield 97%) of 2-chloro-4-(3,7-dimethyloctyl)-4-hydroxy-5-[(Z)-6-methoxycarbonylhexylidene]-4-trimethylsilyloxy-2-cyclopentenone.

NMR (δppm, CDCl$_3$): 0.7–1.0 (9H, m), 1.0–2.0 (18H, m), 2.0–2.6 (4H, m), 2.6–3.1 (1H, m), 3.60 (3H, s), 6.33 (1H, t, J=7.5 Hz), 7.13 (1H, s).

EXAMPLE 7

Production of 2-chloro-4-(3,7-dimethyloctyl)-4-hydroxy-5-[(E)-6-methoxycarbonylhexylidene]-2-cyclopentenone 11 mg (23 micromoles) of 2-chloro-4-(3,7-dimethyloctyl)-5-[(E)-6-methoxycarbonylhexylidene]-4-trimethylsilyloxy-2-cyclopentenone obtained in accordance with Example 5 was dissolved in 0.5 ml of a 3:1:1 mixture of acetic acid, tetrahydrofuran and water, and worked up in the same way as in Example 6 to give 8.6 mg (yield 92%) of 2-chloro-4-(3,7-dimethyl octyl)-4-hydroxy-5-[(E)-6-methoxycarbonylhexylidene]-2-cyclopentenone.

NMR (δppm, CDCl$_3$) 0.7–1.0 (9H, m), 1.0–2.0 (18H, m), 2.0–3.1 (5H, m), 3.59 (3H, s), 6.61 (1H, dd, J=9.0 and 7.0 Hz), 7.20 (1H, s).

EXAMPLE 8

Production of 2-chloro-4-trimethylsilyloxy-4-[3-(3,4-dimethoxyphenyl)propyl]-5-(1-hydroxy-6-methoxycarbonylhexyl)-2-cyclopentenone (1) Production of 4-t-butyldimethylsilyloxy-3-chloro-1-(3,4-dimethoxyphenylpropyl)-1-hydroxy-2-cyclopentene 128 mg (5.3 mmoles) of magnesium was taken, and 4 ml of dry tetrahydrofuran was added. Then, a small amount of a solution of 1.37 g of 1-bromo-3-(3,4-dimethoxyphenyl)propane in 10 ml of dry tetrahydrofuran was added. The mixture was heated. After the initiation of the reaction, a solution of 1-bromo-3-(3,4-dimethoxyphenyl)propane in tetrahydrofuran was added little by little, and the solution was refluxed for 1.5 hours. The resulting reagent was cooled to −78° C., and a cooled solution of 1.305 g of 3-chloro-4-t-butyldimethylsilyloxy-2-cyclopentenone in dry tetrahydrofuran was added. The mixture was stirred at −78° C. for 1.5 hours. A saturated aqueous solution of ammonium chloride was added, and the mixture was extracted with ethyl acetate. The organic layer was washed with a saturated aqueous solution of sodium chloride, and dried over anhydrous sodium sulfate. After filtration and concentration, the residue was chromatographed on a silica gel column to give 600 mg (yield 27%) of 4-t-butyldimethylsilyloxy-3-chloro-1-(3,4-dimethoxyphenylpropyl)-1-hydroxy-2-cyclopentene.

NMR (δppm, CDCl$_3$): 0.10 (6H, s), 0.87 (9H, s), 1.5–2.8 (9H, m), 3.81 (6H, s), 4.6–4.9 (1H, m), 5.72 (1H, s), 6.5–6.9 (3H, m).

(2) Production of 2-chloro-4-(3,4-dimethoxyphenylpropyl)-4-hydroxy-2-cyclopentenone By repeating the procedure of Example 4, (2) using 242 mg of 4-t-butyldimethylsilyloxy-3-chloro-1-(3,4-dimethoxyphenylpropyl)-1-hydroxy-2-cyclopentene obtained by the method indicated in (1) above, 104 mg (yield 59%) of 2-chloro-4-(3,4-dimethoxyphenylpropyl)-4-hydroxy-2-cyclopentenone was obtained.

NMR (δppm, CDCl$_3$) 1.5–2.0 (4H, m), 2.15–2.35 (1H, brs), 2.4–2.8 (4H, m), 3.78 (6H, s), 6.5–6.9 (3H, m), 7.24 (1H, s).

(3) Production of 2-chloro-4-trimethylsillyloxy-4-[3-(3,4-dimethoxyphenyl)propyl]-2-cyclopentenone By repeating the procedure of Example 4, (3) using 235 mg of 2-chloro-4-hydroxy-4-[3-(3,4-dimethoxyphenyl)propyl]-2-cyclopentenone obtained by the method indicated in (2) above, 229 mg (yield 79%) of 2-chloro-4-trimethylsilyloxy-4-[3-(3,4-dimethoxyphenyl)propyl]-2-cyclopentenone was obtained.

NMR (δppm, CDCl$_3$) 0.09 (9H, s), 1.4–1.9 (4H, m), 2.3–2.8 (4H, m), 3.80 (6H, s), 6.4–6.9 (3H, m), 7.24 (1H, s).

(4) Production of 2-chloro-4-trimethylsilyloxy-4-[3-(3,4-dimethoxyphenyl)propyl]-5-(1-hydroxy-6-methoxycarbonylhexyl)-2-cyclopentenone 159 mg of 2-chloro-4-trimethylsilyloxy-4-[3-(3,4-dimethoxyphenylpropyl]-2-cyclopentenone obtained by the method indicated in (3) was dissolved in 5 ml of dry tetrahydrofuran, and the solution was cooled to −78° C. 4.15 ml of a 0.2 M tetrahydrofuran solution of lithium diisopropylamine was added, and the solution was stirred at −78° C. for 1 hour. A solution cooled at −78° C. of 131 mg of methyl 7-oxoheptanoate in 3 ml of dry tetrahydrofuran, and the mixed solution was stirred at −78° C. for 2 hours. A saturated aqueous solution of ammonium chloride was added, and the mixture was extracted with ethyl acetate. The organic layers were combined, washed with a saturated aqueous solution of sodium chloride, and dried over anhydrous magnesium sulfate. After filtration and concentration, the residue was chromatographed on a silica gel column to give 102 mg (yield 45%) of 2-chloro-4-trimethylsilyloxy-4-[3-(3,4-dimethoxyphenyl)propyl]-5-(1-hydroxy-6-methoxycarbonylhexyl)-2-cyclopentenone.

NMR (δppm, CDCl$_3$): 0.18 (9H, s), 1.0–2.1 (12H, m), 2.1–2.8 (6H, m), 3.59 (3H, s), 3.80 (6H, s), 3.5–4.1 (1H, m), 6.5–6.9 (3H, H), 7.2–7.35 (1H, brs).

EXAMPLE 9

Production of 2-chloro-4-hydroxy-4-[3-(3,4-dimethoxyphenyl)propyl]-5-(1-hydroxy-6-methoxycarbonylhexyl)-2-cyclopentenone 15.2 mg (281.micromoles) of 2-chloro-4-trimethylsilyloxy-4-[3-(3,4-dimethoxyphenyl)propyl]-5-(1-hydroxy-6-methoxycarbonylhexyl)-2-cyclopentenone obtained by the method indicated in Example 8 was dissolved in a 3:1:1 mixture of acetic acid, tetrahydrofuran and water, and worked up in the same way as in Example 3. There was obtained 9.2 mg (yield 70%) of 2-chloro-4-hydroxy-4-[3-(3,4-dimethoxyphenyl)propyl]-5-(1-hydroxy-6-methoxycarbonylhexyl)-2-cyclopentenone.

NMR (δppm, CDCl$_3$): 1.0–2.0 (12H, m), 2.0–2.9 (7H, m), 3.60 (3H, s), 3.80 (6H, s), 3.5–4.4 (1H, m), 6.5–6.9 (3H, m), 7.35 and 7.37 (1H, s).

EXAMPLE 10

Production of 2-chloro-4-trimethylsilyloxy-4-[3-(3,4-dimethoxyphenyl)propyl]-5-(1-methanesulfonyloxy-6-methoxycarbonylhexyl)-2-cyclopentenone and 2-chloro-4-trimethylsilyloxy-4-[3-(3,4-dimethoxyphenyl)propyl]-5-(6-methoxycarbonylhexylidene-2-cyclopentenone 46 mg of 2-chloro-4-trimethylsilyloxy-4-[3-(3,4-dimethoxyphenyl)propyl]-5-(1-hydroxy-6-methoxycarbonylhexyl)-2-cyclopentenone was dissolved in 1 ml of pyridine, and 100 microliters of methanesulfonyl chloride was added. The mixture was stirred for 2.5 hours. 150 microliters of 1,8-diazabicyclo[5.4.0]undec-7-ene was added, and the mixture was stirred for 6 hours. A saturated aqueous solution of potassium hydrogen sulfate was added, and the mixture was extracted with ethyl acetate. The organic layers were combined, washed successively with a saturated aqueous solution of sodium hydrogen carbonate and a saturated aqueous solution of sodium chloride. After filtration and concentration, the residue was chromatographed on a silica gel column to give 15 mg (yield 28%) of 2-chloro-4-trimethylsilyloxy-4-[3-(3,4-dimethoxyphenyl)propyl]-5-(1-methanesulfonyloxy-6-methoxycarbonylhexyl)-2-cyclopentenone and 7.7 mg (yield 17%) of 2-chloro-4-trimethylsilyloxy-4-[3-(3,4-dimethoxyphenyl)propyl]-5-(6-methoxycarbonylhexylidene)-2-cyclopentenone.

23

Spectral data of 2-chloro-4-trimethylsilyloxy-4-[3-(3,4-dimethoxyphenyl)propyl]-5-(1-methanesulfonyloxy-6-methoxycarbonylhexyl)-2-cyclopentenone NMR (δppm, CDCl$_3$): 1.0–2.0 (10H, m), 2.0–2.8 (5H, m), 2.94 (3H, s), 3.59 (3H, s), 3.81 (6H, s), 4.6–5.1 (1H, m), 6.5–6.9 (3H, m), 7.1–7.3 (1H, brs).

Spectral data of 2-chloro-4-trimethylsilyloxy-4-[3-(3,4-dimethoxyphenyl)propyl]-5-(6-methoxycarbonylhexylidene)-2-cyclopentenone NMR (δppm, CDCl$_3$): 1.1–2,1 (10H, m), 2.1–2.8 (6H, m), 3.62 (3H, s), 3.82 (6H, s), 6.4–6.8 (3H, m), 7.03 and 7.10 (1H, s).

EXAMPLE 11

Production of 2-chloro-4-trimethylsilyloxy-4-[3-(3,4-dimethoxyphenylpropyl]-5-(6-methoxycarbonylhexylidene)-2-cyclopentenone 15 mg (24.2 micromoles) of 2-chloro-4-trimethylsilyloxy-4-[3-(3,4-dimethoxyphenyl)propyl]-5-(1-methanesulfonyloxy-6-methoxycarbonylhexyl)-2-cyclopentenone obtained by the method indicated in Example 10 was dissolved in 0.5 ml of benzene, and 50 mg (329 micromoles) of 1,8-diazabicyclo[5.4.0]undec-7-ene was added. The mixture was stirred for 2.5 hours. A saturated aqueous solution of sodium chloride was added, and the mixture was extracted with ethyl acetate. The organic layer was washed with a saturated aqueous solution of water, and dried over an hydrous sodium sulfate. After filtration and concentration, the residue was subjected to a thin-layer chromatography to give 8.2 mg (yield 65%) of 2-chloro-4-trimethylsilyloxy-4-[3-(3,4-dimethoxyphenyl)propyl]-5-(6-methoxycarbonylhexylidene)-2-cyclopentene.

EXAMPLE 12

Production of 2-chloro-4-hydroxy-4-[3-(3,4-dimethoxyphenyl)-propyl]-5-(6-methoxycarbonylhexylidene)-2-cyclopentenone 15.9 mg (30.4 micromoles) of 2-chloro-4-trimethylsilyloxy-4-[3-(3,4-dimethoxyphenyl)propyl]-5-(6-methoxycarbonylhexylidene)-2-cyclopentenone obtained by the method indicated in Example 10 or 11 was dissolved in 0.5 ml of a 3:1:1 mixture of acetic acid, tetrahydrofuran and water, and worked up in the same way as in Example 3 to give 12.1 mg (yield 88%) of 2-chloro-4-hydroxy-4-[3-(3,4-dimethoxyphenyl)-propyl]-5-[6-methoxycarbonylhexylidene)-2-cyclopentenone.

NMR (δppm, CDCl$_3$) 1.0–3.2 (17H, m), 3.60 (3H, s), 3.79 (6H, s), 6.0–6.9 (4H, m), 7.07 and 7.13 (1H, s).

EXAMPLE 13

Production of 4-butyl-5-(1-hydroxybutyl)-4-trimethylsilyloxy-2-cyclopentenone (1) Production of 4-butylcyclopent-2-ene-1,4-diol 30 ml of tetrahydrofuran was put in a reaction tube and cooled to −78° C., and n-butyllithium (as a 1.6M hexane solution; 13.8 ml, 22.08 mmmoles) was added dropwise. Then a solution of 4-hydroxy-2-cyclopentenone (987 mg; 10.1 mmoles) in 20 ml of tetrahydrofuran was added dropwise over about 20 minutes. The reaction mixture was washed with 8 ml of tetrahydrofuran. After 60 minutes, 40 ml of a saturated aqueous solution of ammonium chloride was added, and the mixture was vigorously shaken. The organic layer was separated, and the aqueous layer was extracted with ethyl acetate (20 ml×6). The extracts were dried over anhydrous sodium sulfate, filtered and concentrated. The residue was chromatographed on a silica gel column (Merck silica gel 30 g; hexane:ethyl acetate=4:1) to obtain 1.55 g (yield about 90%) of 4-butylcyclopent-2-ene-1,4-diol.

Rf=0.3 (1:6=hexane:ethyl acetate).

NMR (δppm, CDCl$_3$) 0.7–1.0 (3H, t, CH$_3$), 1.1–1.8 (8H, m, CH$_2$ and CH$_2$, OH), 2.0–2.1 (1H, brs, OH), 2.2–2.5 (1H, dd, CH$_2$), 4.5–4.8 (1H, brs, CHOH), 5.7–5.9 (2H, m, vinyl).

(2) Production of 4-hydroxy-4-butyl-2-cyclopentenone 4-butylcyclopent-2-ene-1,4-diol obtained in (1) above (1.33 g, 8.48 mmiles) was weighed into a flask, and about 20 ml of acetone was added. The solution as cooled to 0° C. 2.0 g of a Jones oxidizing agent (prepared from 2.0 g of chromium trioxide, 1.8 ml of conc. sulfuric acid and 5 ml of water) was slowly added dropwise to the solution. About 10 minutes later, a saturated aqueous solution of sodium hydrogen carbonate was added dropwise. The organic layer as separated, and the aqueous layer was extracted with methylene chloride, dried over anhydrous sodium sulfate, filtered and concentrated. The residue was chromatographed on a silicagel column (Merck Silica Gel; hexane:ethyl acetate=3:1). The product was concentrated and subjected to distillation to give 640 mg (yield about 50%) of 4-hydroxy-4-butyl-2-cyclopentenone.

Rf=0.58 (1:6=hexane:ethyl acetate).

NMR (δppm, CDCl$_3$): 0.7–1.0 (3H, t, CH$_3$), 2.5 (2H, d, CH$_2$), 2.6–3.1 (1H, br, OH), 6.1 (1H, d, vinyl), 7.4 (1H, d, vinyl).

(3) Production of 4-butyl-4-trimethylsilyloxy-2-cyclopentenone 4-butyl-4-hydroxy-2-cyclopentenone (73 mg, 0.47 mmole) obtained in (2) above was taken into a flask, and 3 ml of diisopropyl ethylamine was added. The mixture was cooled to 0° C. Trimethylsilyltrifluoromethanesulfonic acid (0.25 M methylene chloride solution, 3.9 ml, 0.96 mmole) was added over about 10 minutes. After about 10 minutes, the reaction mixture was poured into a separating funnel, and water was added. The mixture was then extracted with pentane, dried over anhydrous sodium sulfate, filtered, and concentrated. The residue was chromatographed in a silica gel column (Merck ssilica gel 7 g; hexane:ethyl acetate=30:1) to give 84 mg (yield 78%) of 4-butyl-4-trimethylsilyloxy-2-cyclopentenone.

Rf=0.60 (3:1=hexane:ethyl acetate).

NMR (δppm, CDCl$_3$) 0.07 (9H, s, Si(CH$_3$)$_3$), 0.7–1.1 (3H, t, CH$_3$), 1.1–1.9 (6H, m, CH$_2$), 2.5 (2H, s, CH$_2$), 6.1 (1H, d, vinyl), 7.4 (1H, d, vinyl).

(4) Production of 4-butyl-5-(1-hydroxybutyl)-4-trimethylsilyloxy-2-cyclopentenone In a reacion tube 0.13 ml (0.92 mmole) of diisopropylamine and 0.58 ml (0.92 mmoles) of n-butyllithium (1.6 M, hexane) were added, and 8 ml of a tetrahydrofuran solution of lithium diisopropylethylamine (LDA for short) was prepared. At −78° C., a solution of 161 mg (0.71 mmole) of 4-n-butyl-4-trimethylsilyloxy-2-cyclopentenone obtained in (3) above in 12 ml of tetrahydrofuran was added over 20 minutes. Furthermore, a solution of 0.08 ml (0.92 mmole) of butyraldehyde in 7 ml of tetrahydrofuran was added, and the mixture was stirred for 1.5 hours. A saturated aqueous solution of ammonium chloride (20 ml) was added, and the mixture was extracted with ether. The extract was dried over anhydrous magnesium sulfate, filtered and concentrated. The residue was chromatographed on a silica gel column (Merck silica gel 8 g; hexane:ethyl acetate=40:1) to give 193 mg (yield 91%) of 4-butyl-5-(1-hydroxybutyl)-4-trimethylsilyloxy-2-cyclopentenone.

NMR ($\delta$ppm, CDCl$_3$): 0.15 (9H, s), 0.8–1.1 (6H, m), 1.1–2.0 (10H, m), 2.3 (1H, m), 3.95 (1H, m), 6.1 (1H, d, J=6 Hz), 7.4 (1H, d, J=6 Hz).

EXAMPLE 14

Production of 4-butyl-5-[(E)-butylidene]-4-trimethylsilyloxy-2-cyclopentenone and 4-butyl-5-[(Z)-butylidene]-4-trimethylsilyloxy-2-cyclopentenone 40 mg (0.13 mmole) of 4-butyl-5-(1-hydroxybutyl)-4-trimethylsilyloxy-2-cyclopentenone was dissolved in 2 ml of pyridine, and at room temperature, 0.1 ml (1.3 mmoles) of mesyl chloride was added. The mixture was stirred for 8 hours. After the reaction, water was added, and the mixture was extracted with methylene chloride. The extract was dried, and concentrated, and 2 ml of benzene and 0.2 ml (1.3 mmoles) of DBU were added. The mixture was stirred at room temperature for 2 hours. Water was added, and the mixture was exracted with benzene. The extract was dried and concentrated, and the residue was chromatographed on a silica gel column (Merck silica gel 4 g, hexane:ethyl acetate=20:1) to give 18 mg (yield 48%) of 4-butyl-5-[(E)-butylidene]-4-trimethylsilyloxy-2-cyclopentenone (Rf=0.7, hexane:ethyl actate=3:1) and 5 mg (yield 14%) of its Z-isomer (Rf=0.75, hexane:ethyl acetate=3:1).

NMR ($\delta$ppm, CDCl$_3$):
<E -isomer>
0.1 (9H, s), 0.7–1.0 (6H, m), 1.0–2.0 (8H, m), 2.2–2.5 (2H, m), 6.3 (1H, d, J=6 Hz), 6.5 (1H, d, t, J=1 Hz and 7 Hz), 7.3 (1H, dd, J=1 Hz and 6 Hz).
<Z-isomer>
0.1 (9H, s), 0.7–1.0 (6H, m), 1.0–1.9 (8H, m), 2.6–2.9 (2H, m), 6.0–6.2 (2H, m), 7.2 (1H, d, J=6 Hz).

EXAMPLE 15

Production of 4-butyl-5-[(E)-butylidene]-4-hydroxy-2-cyclopentenone 10 mg (0.035 mmole) of 4-butyl-5-[(E)-butylidene-4-trimethylsilyloxy-2-cyclopentenone was dissolved in 3 ml of tetrahydrofuran, and at 0° C., 0.14 ml (0.14 mmole) of tributyl ammonium fluoride was added. The mixture was stirred for 40 minutes. A saturated aqueous solution of sodium chloride was added, and the mixture was extracted with ethyl acetate. The extract was dried and concentrated, and the residue was chromatographed on a silica gel column (Merck silica gel 4 g; hexane:ethyl acetate=4:1) to give 5 mg (yield 70%) of 4-butyl-5-[(E)-butylidene]-4-hydroxy-2-cyclopentenone.

NMR ($\delta$ppm, CDCl$_3$): 0.7–1.0 (6H, m), 1.0–2.1 (8H, m), 2.2–2.5 (2H, m), 6.3 (1H, d, J=6 Hz), 6.6 (1H, t, J=7 Hz), 7.3 (1H, d, J=6 Hz).

EXAMPLE 16

Production of 4-butyl-5-[(Z)-butylidene]-4-hydroxy-2-cyclopentenone

In the same way as in Example 15, 2.7 mg (yield 68%) of 4-butyl-5-[(1Z)-butylidene]-4-hydroxy-2-cyclopentenone was obtgained from 5.3 g (0.019 mmole) of 4-butyl-5-[(Z)-butylidene)-4-trimethylsilyloxy-2-cyclopentenone and 0.07 ml 0.07 mmole) of tetrabutyl ammonium fluoride.

NMR ($\delta$ppm, CDCl$_3$): 0.7–1.0 (6H, m), 1.0–2.0 (8H, m), 2.6–2.9 (2H, m), 6.1–6.3 (1H, m), 7.2 (1H, d, J=6 Hz).

EXAMPLE 17

Production of 4-trimethylsilyloxy-5-(1-hydroxy-6-methoxycarbonylhexyl)-4-octyl-2-cyclopentenone Under a nitrogen atmosphere at −78° C., a solution of 200 mg (0.71 mmole) of (4R)-4-trimethylsilyloxy-4-octyl-2-cyclopentenone in 2 ml of tetrahydrofuran was added to a solution of LDA prepared from 93 mg (0.92 mmole) of isopropylamide and 590 microliters of n-butyllithium (as a 10 W/V % hexane solution) in 3 ml of tetrahydrofuran, and the mixture was stirred for 1 hour. Then, a solution of 146 mg (0.92 mmole) of methyl 6-formylhexanoate in 2 ml of tetrahydrofuran was added, and the mixture was stirred at −78° C. for 2 hours. The reaction was terminated by adding an aqueous solution of ammonium chloride. The reaction mixture was extracted with ether, and the extract was dried over anhydrous magnesium sulfate, filtered and concentrated.

The residue was chromatographed on a thin silica gel column (n-hexane:ethyl acetate=3:1) to recover 21 mg of the starting material (Rf=0.75) and obtain 41 mg (13%) of a mixture of a low polarity portion (FrA) (Rf=0.68) and a medium polarity portion (FrB) (Rf=0.6), and 221 mg (71%) of a low polarity portion (FrC) (Rf=0.5).

FrA, FrB and FrC (mixture) correspond to the following.
<FrA>
NMR ($\delta$ppm, CDCl$_3$): 0.05 (9H, s), 0.7–1.1 (3H, m), 1.1–2.1 (22H, m), 2.1–2.4 (3H, m), 3.6 (3H, s), 4.3 (1H, m), 6.0 (1H, d, J=6 Hz), 7.4 (1H, d, J=6 Hz).
<FrB>
NMR ($\delta$ppm, CDCl$_3$): 1.0 (9H, s), 0.7–1.1 (3H, m), 1.1–2.0 (22H, m), 2.1–2.5 (3H, m), 3.6 (3H, s), 4.1 (1H, m), 6.0 (1H, d, J=6 Hz), 7.35 (1H, d, J=6 Hz).
<FrC>
NMR ($\delta$ppm, CDCl$_3$): 2.0 (9H, s), 0.7–1.1 (3H, m), 1.1–2.0 (22H, m), 2.0–2.5 (3H, m), 3.6 (3H, s), 3.2–4.0 (2H, m), 6.05 (1H, d, J=6 Hz), 7.25 (1H, d, J=6 Hz).

IR (cm$^{-1}$, neat): 3500, 2950, 2870, 1740, 1710, 1460, 1440, 1350, 1255.

EXAMPLE 18

Production of (4R)-5-(6-methoxycarbonylhexylidene)-4-trimethylsilyloxy-4-octyl-2-cyclopentenone 188 mg (0.43 mmole) of (4R)-5-(1-hydroxy-6-methoxycarbonylhexyl)-4-trimethylsilyloxy-4-octyl-2-cyclopentenone was dissolved in 3 ml of pyridine, and at 0° C., 160 microliters (2.15 mmoles) of mesyl chloride was added. The mixture was stirred at room temperature for 2 hours. Then, 0.5 ml of DBU was added, and the mixture was stirred at room temperature for 2 hours. Water was added to terminate the reaction, and the reaction mixture was extracted with ether. The organic layer was washed with aqueous solutions of potassium hydrogen sulfate, sodium hydrogen carbonate and sodium chloride. After filtration and concentration, the residue was subjected to TLC (n-hexane:AcOEt=3.5:1) to obtain 27 mg (15%) of a low polarity product (Z-isomer) and 113 mg (63%) of a high polarity product (E-isomer).

<E-isomer>

Rf=0.55 (n-hexane:AcOEt=3:1).

NMR (δppm, CDCl$_3$): 0.05 (9H, s), 0.7–1.0 (3H, m), 1.0–1.4 (12H, m), 1.4–2.1 (8H, m), 2.1–2.6 (4H, m), 3.6 (3H, s), 6.2 (1H, d, J=6 Hz). 6.45 (1H, t, J=7.5 Hz), 7.20 (1H, d, J=6 Hz).

IR (cm$^{-1}$, neat): 2950, 2870, 1740, 1710, 1660, 1460, 1440, 1360, 1250.

<Z-isomer>

Rf=0.6 (n-hexane:AcOEt=3:1).

NMR (δppm, CDCl$_3$): 0.05 (9H, s), 0.7–1.0 (3H, m), 1.0–1.9 (20H, m), 2.0–2.45 (2H, m), 2.45–2.9 (2H, m), 3.55 (3H, s), 6.0 (1H, t, J=75 Hz). 6.1 (1H, d, J=6 Hz), 7.1 (1H, d, J=6 Hz).

IR (cm$^{-1}$, neat): 2950, 2870, 1740, 1700, 1650, 1460, 1440, 1360, 1340, 1250, 1200.

EXAMPLE 19

Production of (4R)-5-[(E)-6-methoxycarbonylhexylidene)-4-hydroxy-4-octyl-2-cyclopentenone 113 mg (0.27 mmole) of (4R)-5-[(E)-6-methoxycarbonylhexylidene)-4-octyl-4-trimethylsilyloxy-2-cyclopentenone was dissolved in 20 ml of tetrahydrofuran, and at 0° C., 1 ml (1 mmole) of n-Bu$_4$NF (1 M in THF) was added. The mixture was stirred for 15 minutes. Ether and a saturated aqueous solution of sodium chloride were added. The aqueous layer was extracted with ethyl acetate. After filtration and concentration, the residue was subjected to TLC (n-hexane:AcOEt=1:1) to obtain 31 mg (33%) of (4R)-5-[(E)-6-methoxycarbonylhexylidene)-4-hydroxy-4-octyl-2-cyclopentenone.

Rf=0.5 (n-hexane:AcOEt=1:1).

NMR (δppm, CDCl$_3$): 0.65–1.00 (3H, m), 1.00–1.3 (12H, m), 1.3–2.7 (12H, m), 3.55 (3H, s), 6.15 (1H, d, J=6 Hz), 6.35 (1H, t, J=8 Hz), 7.20 (1H, d, J=6 Hz).

IR (cm$^{-1}$, neat): 3450, 2950, 2880, 1740, 1710, 1640, 1360, 1340.

EXAMPLE 20

Production of (4R)-5-[(Z)-6-methoxycarbonylhexylidene)-4-hydroxy-4-octyl-2-cyclopentenone By operating in the same way as in Example 19 using 55 mg (0.13 mmole) of (4R)-5-[(Z)-6-methoxycarbonylhexylidene)-4-octyl-4-trimethylsilyloxy-2-cyclopentenone, 37 mg (81%) of (4R)-5-[(Z)-6-methoxycarbonylhexylidene)-4-hydroxy-4-ocyl-2-cyclopentenone was obtained.

Rf=0.55 (n-hexane:AcOEt=1:1).

NMR (δppm, CDCl$_3$): 0.7–1.0 (3H, m), 1.0–2.0 (20H, m), 2.0–2.9 (5H, m), 3.55 (3H, s), 6.1 (1H, t, J=7 Hz), 6.1 (1H, d, J=6 Hz), 7.1 (1H, d, J=6 Hz).

IR (cm$^{-1}$, neat): 3450, 2950, 2870, 1740, 1700, 1650, 1460, 1440, 1360, 1260, 1200.

EXAMPLE 21

Production of 4-butyl-2-chloro-5-(1-hydroxy-6-methoxycarbonylhexyl)-4-trimethylsilyloxy-2-cyclopentenone 54 mg of 4-butyl-4-t-butyldimethylsilyloxy-2-chloro-2-cyclopentenone was dissolved in 2 ml of dry tetrahydrofuran, and the solution was cooled to −78° C. With stirring, a lithium diisopropyl amide solution was added. At −78° C., the mixture was stirred for 30 minutes. A solution of 50 mg of methyl 7-oxoheptanoate in 1 ml of dry tetrahydrofuran was added, and the mixed solution was stirred at −78° C. to −50° C. for 1 hour. A saturated aqueous solution of ammonium chloride was added, and the mixture was extracted with ethyl acetate. The organic layer was washed with a saturated aqueous solution of sodium chloride, and dried over anhydrous sodium sulfate. After filtration and concentration, the residue was chromatographed on a silica gel column (silica gel 30 g; hexane:ethyl acetate=50:1→10:1) to give 29 mg (yield 33%) of a low polarity isomer of 4-butyl-2-chloro-5-(1-hydroxy-6-methoxycarbonylhexyl)-4-trimethylsilyloxy-2-cyclopentenone and 17 mg (yield 20%) of its high polarity isomer.

<low polarity isomer>

Rf=0.39 (hexane:ethyl acetate=5:1).

IR (cm$^{-1}$, neat): 3460, 1729, 1602, 1256, 842.

NMR (δppm, CDCl$_3$): 0.04 (9H, s), 0.87 (3H, t, J=4.6 Hz), 1.0–2.1 (14H, m), 2.1–2.5 (3H, m), 3.59 (3H, s), 4.30 (1H, brt, J=7.0 Hz), 4.80 (1H, brs), 7.39 (1H, s).

<high polarity isomer>

Rf=0.32 (hexane:ethyl acetate=5:1).

IR (cm$^{-1}$, neat): 3480, 1730, 1604, 1253, 838.

NMR (δppm, CDCl$_3$): 0.13 (9H, s), 0.87 (3H, t, J=4.6 Hz), 1.0–2.0 (14H, m), 2.1–2.5 (2H, m), 2.51 (1H, d, J=4.0 Hz), 3.57 (3H, s), 3.87 (1H, s), 3.8–4.4 (1H, m), 7.39 (1H, s).

EXAMPLE 22

Production of 5-(4,7-di-t-butyldimethylsilyloxy-1-hydroxy-2-hepten-1-yl)-4-(4-phenoxybutyl)-4-trimethylsilyloxy-2-cyclopentenone (1) Production of 5-t-butyldimethylsilyloxy-3-hydroxy-3-(4-phenoxybutyl)cyclopentenone 55 ml (39 mmoles) of a 0.71 M solution of 4-phenoxybutyl magnesium bromide prepared from 10.1 g (44 mmoles) of 4-phenoxy bromide and 1.07 g (44 mmoles) of magnesium in 60 ml of ether was taken, and in an atmosphere of nitrogen, a solution of 7.63 g (36 mmoles) of 4-t-butyldimethylsilyloxy-2-cyclopentenone in 20 ml of ether was added dropwise at −78° C., and the mixture was stirred for 4 hours. A saturated aqueous solution of sodium chloride was added to terminate the reaction. The reaction mixture was extracted with ether, washed with an aqueous sodium chloride solution, dried over anhydrous magnesium sulfate, filtered, and concentrated. The residue was chromatographed on a silica gel column (hexane:AcOEt=12:1) to give 5.2 g (40%) of a low polarity, 1,2-adduct and 2.9 g (22%) of a high polarity 1,2-adduct.

Low polarity 1,2-adduct ( 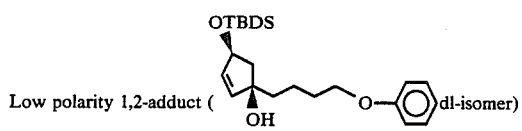 dl-isomer)

NMR (δppm, CDCl₃): 0.1 (6H, s), 0.9 (9H, s), 1.2–2.0 (6H, m), 1.91 (1H, d, J=14 Hz), 2.35 (1H, dd, J=14 Hz and 6 Hz), 3.9 (2H, m), 4.6 (1H, dd, J=6 Hz and 4 Hz), 5.75 (2H, s), 6.65–7.4 (5H, m).

IR (cm⁻¹, neat): 3450, 2950, 2870, 1740, 1600, 1590, 1360, 1300, 1250, 1090.

High polarity 1,2-adduct ( 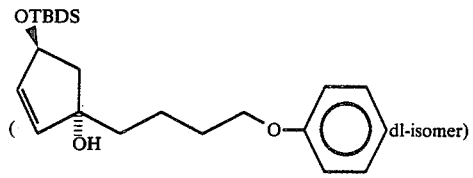 dl-isomer)

NMR (δppm, CDCl₃): 0.1 (6H, s), 0.9 (9H, s), 1.2–2.5 (8H, m), 3.85 (2H, m), 4.9 (1H, dd, J=6 Hz and 4 Hz), 5.75 (2H, s), 6.65–7.3 (5H, m).

IR (cm⁻¹, neat): 3450, 2950, 2870, 1740, 1600, 1590, 1360, 1300, 1250, 1100.

(2) Production of 4-(4-phenoxybutyl)cyclopent-2-ene-1,4-diol 8 g (22 mmoles) of 5-t-butyldimethylsilyloxy-3-hydroxy-3-(4-phenoxybutyl)cyclopentenone was dissolved in 25 ml of tetrahydrofuran, and 11 g (35 mmoles) of n-Bu₄NF.3H₂O was added. The mixture was stirred at room temperature for 4 hours. After the addition, a saturated sodium chloride solution and ether were added. The aqueous layer was extracted with ethyl acetate. The extract was dried over anhydrous magnesium sulfate. After filtration and concentration, the residue was chromatographed on a silica gel column (hexane:AcOEt=1:2) to give 37 g (68%) of 4-(4-phenoxybutyl)cyclopent-2-ene-1,4-diol.

NMR (δppm, CDCl₃): 1.2–2.1 (7H, m), 2.35 (1H, dd, J=14 Hz and 7 Hz), 3.85 (2H, m), 4.5 and 4.85

( 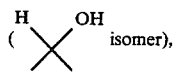 isomer), (1H, both m), 5.75 (2H, s), 6.6–7.3 (5H, m).

(3) Production of 4-hydroxy-4-(4-phenoxybutyl)-2-cyclopentenone 1.9 g (7.6 mmoles) of 3,5-dihydroxy-3-(4-phenoxybutyl)cyclopentene was dissolved in 15 ml of dichloromethane, and at 0° C. 5.7 g (15 mmoles) of pyridinium dichromate was added. The mixture was stirred at room temperature for 2 hours. The reaction mixture was diluted with 200 ml of ether, and filtered through Celite. After concentration, 1.32 g (71%) of 4-hydroxy-4-(4-phenoxybutyl)-2-cyclopentenone was obtained.

NMR (δppm, CDCl₃): 1.3–2.1 (6H, m), 2.4 (2H, s), 3.85 (2H, m), 5.95 (1H, d, J=5 Hz), 7.30 (1H, d, J=5 Hz), 6.65–7.4 (5H, m).

IR (cm⁻¹, neat): 3450, 2950, 2900, 1715, 1680, 1600, 1590, 1400, 1290, 1250, 1170.

(4) Production of 4-(4-phenoxybutyl)-4-trimethylsilyloxy-2-cyclopentenone

A solution of 1.2 g (4.9 mmoles) of 4-hydroxy-4-(4-phenoxybutyl)-2-cyclopentenone in 10 ml of diisopropylethylamine was cooled to 0° C. in an atmosphere of nitrogen, and 20 ml (10 mmoles) of trimethylsilyl trifluoromethanesulfonate (5 M dichloromethane solution) was added. The mixture was stirred for 20 minutes. After the reaction, water was added, and the mixture was exracted with ether. The extract was washed with water and an aqueous sodium chloride solution, and then dried. The solvent was distilled off under reduced pressure. The residue was chromatographed on a silica gel column (n-hexane:AcOEt=10:1) to give 1.2 g (77%) of 4-(4-phenoxybutyl)-4-trimethylsilyloxy-2-cyclopentenone.

NMR (δppm, CDCl₃): 0.1 (9H, s), 1.6 (6H, m), 2.45 (2H, s) 3.9 (2H, m), 6.05 (1H, d, J=6 Hz), 6.7–7.4 (5H, m), 7.4 (1H, d, J=6 Hz).

(5) Production of 5-(4,7-di-t-butyldimethylsilyloxy-1-hydroxy-2-hepten-1-yl)-4-(4-phenoxybutyl)-4-trimethylsilyloxy-2-cyclopentenone 100 mg (0.31 mmole) of 4-(4-phenoxybutyl)-4-trimethylsilyloxy-2-cyclopentenone was dissolved in 4 ml of ether, and the solution was cooled to −78° C. Diisoproylethylamine (82 microliters; 0.47 mmole) and then 0.47 ml (0.47 mmole) of diisobutylboron trifluoromethanesulfonate (1 M dichloromethane solution) were added. The mixture was stirred for 30 minutes, and then a solution of 186 ml (0.5 mmole) in 2 ml of ether was added, and the mixture was stirred for 4 hours. The reaction was terminated by adding an aqueous solution of ammonium chloride, and the reaction mixture was extracted with ether. The extract was washed with an aqueous solution of sodium hydrogen carbonate, water and an aqueous sodium chloride solution, and chromatographed on a silica gel column (n-hexane:AcOEt=15:1) to give 185 g (85%) of 5-(4,5-di-t-butyldimethylsilyloxy-1-hydroxy-2-hepten-1-yl)-4-(4-phenoxybutyl)-4-trimethylsilyloxy-2-cyclopentenone.

NMR (δppm, CDCl₃): 0.1 (15H, s), 0.9 (18H, s), 1.2–2.0 (10H, m), 2.5 (1H, m), 3.5 (2H, m), 3.95 (3H, m), 4.45 (1H, m), 5.75 (2H, m), 6.1 (1H, d, J=6 Hz), 6.6–7.5 (5H, m), 6.55 (1H, d, J=6 Hz).

EXAMPLE 23

Production of 5-(4,7-di-t-butyldimethylsilyloxy-2-pentenylidene)-4-(4-phenoxybutyl)-4-trimethylsilyl oxy-2-cyclopentenone 177 mg (0.25 mmole) of 5-(4,7-di-t-butyldimethylsilyloxy-1-hydroxy-2-hepten-1-yl)-4-(4-phenoxybutyl)-4-trimethylsilyloxy-2-cyclopentenone was dissolved in 5 ml of dry pyridine, and 99 microliters (1.25 mmoles) of methanesulfonyl chloride was added at 0° C. The mixture was stirred for 4 hours at room temperature. Water and ether were added to extract the reaction mixture. The extract was washed with sodium hydrogn carbonate, potassium hydrogen sulfate, an aqueous sodium chloride solution and water. The product was separated by TLC (n-hexane:ACOEt=3:1) together with a product obtained from 10 mg of the starting material. The following compounds were obtained.

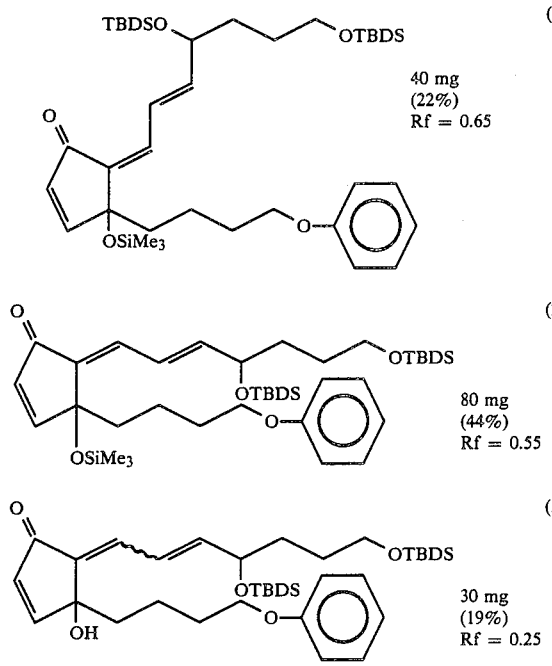

The spectral data of these compounds were as follows:

Compound (1)

NMR (δppm, CDCl₃, 60 MHz): 0.85 (18H, s), 1.1–2.1 (10H, m), 3.55 (2H, m), 3.85 (2H, m), 4.25 (1H, m), 6.0–8.0 (10H, m).

Compound (2)

NMR (δppm, CDCl₃, 60 MHz): 0.9 (18H, s), 1.0–2.2 (10H, m), 3.55 (2H, m), 3.85 (2H, m), 4.3 (1H, m), 6.0–7.6 (10H, m).

IR (cm⁻¹, neat): 2960, 2950, 2870, 1700, 1640, 1600, 1590, 1500, 1470, 1250, 1100.

Compound (3)

NMR (δppm, CDCl₃, 60 MHz): 0.9 (18H, s), 1.0–2.2 (10H, m), 3.60 (2H, m), 3.9 (2H, m), 4.35 (1H, m), 5.9–8.0 (10H, m).

EXAMPLE 24

Production of
5-[(Z)-4,7-dihydroxy-2E-pentenylidene]-4-(4-phenoxybutyl)-4-hydroxy-2-cyclopentenone 30 mg (0.045 mmole) of the starting trisilyl compound was dissolved in 5 ml of a mixture of AcOH:THF:H₂O (=3:1:1), and the solution was stirred at 40° C. for 4 hours. After the reaction, toluene was added, and AcOH and water were dissilled off. The residue was chromatographed on a silica gel column (AcOEt→AcEt, 10% MeOH) together with a crude product obtained from 6 mg of the trisilyl compound to obtain 14 mg (70%) of a triol compound indicated above.

NMR (δppm, CDCl₃, 60 MHz): 1.1–2.2 (10H, m), 3.4–4.1 (7H, m), 4.3 (1H, m), 6.0–7.9 (10H, m).

IR (cm⁻¹, neat): 3350, 2950, 2900, 1685, 1630, 1600, 1500, 1470, 1240, 1170.

EXAMPLE 25

Production of
5-[(E)-4,7-dihydroxy-2E-pentenylidene]-4-(4-phenoxybutyl)-4-hydroxy-2-cyclopentenone 80 mg (0.12 mmole) of the trisilyl compound was dissolved in 10 ml of a mixture of AcOH:THF:H₂O (=3:1:1), and the solution was stirred for 4 hours at 40° C. After the reaction, toluene was added, and AcOH and water were distilled off. The residue was chromatographed on a silica gel column (AcOEt→AcOEt, 10% MeOH) to give 40 mg (90%) of a triol compound indicated above.

NMR (δppm, CDCl₃, 60 MHz): 1.0–2.2 (10H, m), 3.4–4.5 (8H, m), 6.0–6.4 (1H, m), 6.3 (1H, d, J=6 Hz), 6.7–7.4 (8H, m).

IR (cm⁻¹, neat): 3350, 2950, 2900, 1690, 1630, 1600, 1590, 1500, 1470, 1250.

EXAMPLE 26

Production of
4-(4-phenoxybutyl)-4-trimethylsilyloxy-5-(3,7-dimethyl-1-hydroxy-2,6-octadiene)2-cyclopentenone 100 mg (0.31 mmole) of 4-(4-phenoxybutyl)-4-trimethylsilyloxy-2-cyclopentenone was dissolved in 4 ml of ether, and under a nitrogen stream, the solution was cooled to −78° C. 82 microliters (0.47 mmole) of diisopropylethylamine was added, and further, 0.47 ml (0.47 mmole) of dibutylboron trifluoromethanesulfonic acid (1 M dichloromethane solution) was added. The mixture was stirred for 30 minutes and a solution of 76 mg (0.5 mmole) of citral in 500 microliters of ether was added, and the solution was stirrred at −78° C. The reaction was terminated by adding an aqueous solution of ammonium chloride, and the reaction mixture was extracted with ether. The extract was washed with an aqueous sodium hydrogen carbonate, water and a saturated aqueous solution of sodium chloride, and dried. The solvent was distilled off, and the residue was chromatographed on a silica gel column (n-hexane:AcOEt=5:1) to give 75 mg (51%) of the desired product indicated above.

NMR (67 ppm, CDCl₃): 0.1 (9H, s), 1.3–2.0 (15H, m), 2.0–2.4 (4H, m), 2.6 (1H, d, J=9 Hz), 3.85 (2H, m), 4.65 (1H, dd, J=9 Hz), 5.0 (1H, m), 5.3 (1H, d, J=9 Hz), 6.1 (1H, d, J=6 Hz), 6.65–7.4 (5H, m), 7.45 (1H, d, J=6 Hz).

4-(4-Phenoxybutyl)-4-hydroxy-5-(3,7-dimethyl-1-hydroxy-2,6-octadiene)-2-cyclopentenone was prepared as in Example 25.

EXAMPLE 27

Production of 4-(4-phenoxybutyl)-4-trimethylsilyloxy-5-(3,7-dimethyl-2,6-octadienylidene)-2-cyclopentenone 70 mg (0.15 mmole) of 4-(4-phenoxybutyl)-4-trimethylsilyloxy-5-(3,7-dimethyl-1-hydroxy-2,6-octadiene)-2-cyclopentenone was dissolved in 3 ml of dry pyridine, and at 0° C., 48 microliters (0.62 mmole) of mesyl chloride was added. The mixture was stirred at room temperature for 4 hours. Water and ether were added to extract the reaction mixture. The extract was washed with an aqueous solution of sodium hydrogen carbonate, an aqueous solution of potassium hydrogen sulfate, brine and water. The product was chromatographed on a silica gel column (n-hexane:AcOEt=5:1) to give 54 mg (81%) of the desired compound indicated above.

NMR (δppm, CDCl$_3$): 0.1 (9H, s), 1.3–2.0 (15H, m), 20–2.4 (4H, m), 3.9 (2H, m), 5.1 (1H, m), 6.0–7.7 (9H, m).

EXAMPLE 28

Production of
4-(4-phenoxybutyl)-4-hydroxy-5-(3,7-dimethyl-2,6-octadienylidene)-2-cyclopentenone 50 mg (0.11 mmole) of 4-(4-phenoxybutyl)-4-trimethylsilyloxy-5-(3,7-dimethyl-2,6-octadienylidene)-2-cyclopentenone was dissolved in 10 ml of a mixture of AcOH:THF:H$_2$O (=3:1:1), and the solution was stirred at 40° C. for 3 hours. After the reaction, toluene was added, and AcOH and water were distilled off under reduced pressure. The residue was chromatographed on a silica gel column (hexane:AcOET=1.5:1) to give 32 mg (75%) of the desired compound indicated above.

NMR (δppm, CDCl$_3$): 1.3–2.0 (15H, m), 2.0–2.4 (4H, m), 3.9 (2H, m), 5.1 (1H, m), 6.0–7.6 (9H, m).

EXAMPLE 29

Production of
2-chloro-4-(4-phenoxybutyl)-4-trimethylsilyloxy-5-(3,7-dimethyl-1-hydroxy-2,6-octadiene)-2-cyclopentenone (1) A solution of 246 mg (1 mmole) of 3-chloro-4-t-butyldimethylsilylolxy-2-cyclopentenone in 5 ml of ether was added at −78° C. to a solution of 4-phenoxybutyllithium prepared from 1 equivalent of 4-phenoxybutyl bromide and 2 equivalents of t-butyllithium at −78° C. in 10 ml of ether. The mixture was stirred for 1.5 hours, and an aqueous solution of ammonium chloride was added. The reaction mixture was extracted with ether, dried over anhydrous magnesium sulfate, and concentrated. The resulting oily product was dissolved in 10 ml of tetrahydrofuran, and 2.4 ml of a 1 M tetrahydrofuran solution of tetrabutyl ammonium fluoride was added. The mixture was stirred for 10 hours. A saturated aqueous solution of sodium chloride was added to the reaction mixture, and the mixture was extracted with ethyl acetate. The extract was dried over anhydrous sodium sulfate and concentrated. The concentrate was chromatographed on a silica gel column to give 237 mg (84%) of 2-chloro-4-(4-phenoxybutyl)cyclopent-2-ene-1,4-diol.

(2) Production of
2-chloro-4-hydroxy-4-(4-phenoxybutyl)-2-cyclopentenone 850 mg of 2-chloro-4-(4-phenoxybutyl)-2-cyclopentan-1,4-diol obtained in accordance with (1) above was dissolved in 8 ml of dichloromethane, and 1.8 g of pyridinium dichromate was added. The mixture was stirred for 15 hours, and filtered. A saturated aqueous solution of sodium chloride was added to the filtrate, and the mixture was extracted with ether. The extract was dried over anhydrous magnesium sulfate, and concentrated. The concentrate was chromatographed on a silica gel to give 625 mg (74%) of 2-chloro-4-hydroxy-4-(4-phenoxybutyl)-2-cyclopentenone.

NMR (δppm, CDCl$_3$): 1.3–2.0 (7H, m), 2.65 (2H, m), 3.9 (2H, m), 7.3 (1H, s), 6.7–7.3 (5H, m).

(3) Production of
2-chloro-4-(4-phenoxybutyl)-4-trimethylsilyloxy-2-cyclopentenone A solution of 620 mg (2.2 mmoles) of 2-chloro-4-hydroxy-4-(4-phenoxybutyl)-2-cyclopentenone obtained in accordance with (2) above in 5 ml of diisopropylethylamine was cooled to 0° C. in a stream of nitrogen, and 10 ml (5 mmoles) of trimethylsilyl trifluoromethanesulfonate (0.5 M dichloromethane solution) was added. The mixture was stirred for 20 minutes. After the reaction, water was added, and the mixture was extracted with ether. The extract was dried over anhydrous magnesium sulfate, and the solvent was distilled off. The residue was chromatographed on a silica gel column to give 642 g (83%) of 2-chloro-4-(4-phenoxybutyl)-4-trimethylsilyloxy-2-cyclopentenone.

NMR (δppm, CDCl$_3$): 0.1 (9H, s), 1.3–2.0 (6H, m), 2.65 (2H, s), 3.9 (2H, m), 7.35 (1H, s), 6.7–7.4 (5H, m).

(4) Production of
2-chloro-4-(4-phenoxybutyl)-4-trimethylsilyloxy-5-(3,7-dimethyl-1-hydroxy-2,6-octadiene)-2-cyclopentenone 220 mg (0.62 mmole) of 2-chloro-4-(4-phenoxybutyl)-4-trimethylsilyloxy-2-cyclopentenone was dissolved in 8 ml of ether, and the solution was cooled to −78° C. in a stream of nitrogen. Then, 164 microliters (0.94 mmole) of diisopropylethylamine was added. Further, 0.94 ml (0.94 mmole) of dibutylboron trifluoromethanesulfonic acid (1 M dichloromethane solution) was added. The mixture was stirred for 40 minutes, and a solution of 152 mg (1 mmole) of citral in 1 ml of ether was added. The mixture was stirred at −78° C. The reaction was terminated by adding an aqueous solution of ammonium chloride, and the reaction mixture was extracted with ether. The extract was washed with an aqueous solution of sodium hydrogen carbonate and a saturated aqueous solution of sodium chloride and dried. The solvent was distilled off, and the residue was chromatographed on a silica gel column to obtain 192 mg (61%) of the desired compound indicated above.

NMR (δppm, CDCl$_3$): 0.1 (9H, s), 1.3–2.0 (15H, m), 2.0–2.4 (4H, m), 2.65 (1H, m), 3.9 (2H, m), 4.65 (1H, dd, J=9 Hz), 5.0 (1H, m), 5.3 (1H, d, J=9 Hz), 6.65–7.4 (6H, m).

EXAMPLE 30

Production of
2-chloro-4-(4-phenoxybutyl)-4-hydroxy-5-(3,7-dimethyl-2,6-octadienylidene)-2-cyclopentenone 180 mg (0.37 mmole) of 2-chloro-4-(4-phenoxybutyl)-4-trimethylsilyloxy-5-(3,7-dimethyl-1-hydroxy-2,6-octadiene)-2-cyclopentenone was dissolved in 8 ml of dry pyridine, and at 0° C., 96 microliters (1.24 mmoles) of mesyl chloride was added. The mixture was stirred at room temperature for 5 hours. Water and ether were added to the reaction mixture to extract it. The extract was washed with an aqueous solution of sodium hydrogen carbonate, an aqueous solution of potassium hydrogen sulfate, brine and water. The resulting oily product was dissolved in 20 ml of a mixture of AcOH:THF:H$_2$O (=3:1:1), and the solution was stirred at 40° C. for 3 hours. After the reaction, toluene was added, and AcOH and water were distilled off under reduced pressure. The residue was chromatographed on a silica gel column to give 75 mg (51%) of the desired product indicated above.

NMR (δppm, CDCl$_3$): 1.3–2.0 (15H, m), 2.0–2.4 (4H, m), 3.9 (2H, m), 5.1 (1H, m), 6.0–7.6 (8H, m).

EXAMPLE 31

Measurement of the action of inhibiting Proliferation of L1210 leukemia cell

L1210 leukemia cells were added to an RPMI medium containing 10% FCS (fetal calf serum), and the concentration of the cells was adjusted to $1 \times 10^5$ cells/min. Each of the test compounds shown in Table I was dissolved in 99.5% ethanol. Prior to use, the final concentration of the ethanol solution was adjusted to less than 0.1%, and it was added to the culture medium. The culture medium was then maintained at 37° C. in a stationary condition for 4 days. After the cultivation, the number of surviving cells was measured by dyeing with trypan blue. As a control, 0.1% ethanol was used. A dose-reaction curve plotted from the ratios of proliferation against the control, and $IC_{50}$ was determined.

The results are shown in Table I.

TABLE I

| Test compound (Compound No.) | $IC_{50}$ ($\mu$g/ml) |
|---|---|
| (152) | 0.06 |
| (226) | 0.2 |
| (148) | 1.5 |
| (228) | 0.4 |
| (154) | 0.03 |
| (156) | 0.035 |
| (158) | 0.025 |
| (142) | 0.15 |
| (144) | 0.15 |

EXAMPLE 32

Measurement of the antitumor effect on P338 mouse leukemia tumor $1 \times 10^5$ P388 mouse leukemia cells were intraperitoneally administered to ICR mice. After the lapse of 24 hours, each of the test compounds shown in Table II was intraperitoneally administered to the mice for 5 days. The periods of survival of these animals were examined and the increase of their life span (ILS%) were determined.

The results are shown in Table II.

TABLE II

| Test compound (Compound No.) | Dose (mg/kg/day) | Survival (days) | ILS (%) |
|---|---|---|---|
| (154) | 10 | 10.5 ± 0.8 | 7.1 |
|  | 0 | 9.8 ± 0.4 |  |
| (226) | 5 | 11.0 ± 0 | 10.0 |
|  | 0 | 10.0 ± 0 |  |
| (148) | 10 | 12.7 ± 0.7 | 29.6 |
|  | 5 | 13.0 ± 1.4 | 32.7 |
|  | 2.5 | 11.3 ± 0.5 | 15.3 |
|  | 0 | 9.8 ± 0.4 |  |
| (228) | 15 | 10.2 ± 0.9 | 4.1 |
|  | 0 | 9.8 ± 0.4 |  |
| (152) | 10 | 11.7 ± 1.1 | 19.4 |
|  | 0 | 9.8 ± 0.4 |  |
| (142) | 10 | 11.3 ± 0.5 | 15.3 |
|  | 5 | 10.3 ± 0.5 | 5.4 |
|  | 0 | 9.8 ± 6.4 |  |
| (144) | 15 | 11.7 ± 0.5 | 12.5 |
|  | 10 | 12.2 ± 1.2 | 17.3 |
|  | 5 | 10.7 ± 0.5 | 2.9 |
|  | 0 | 10.4 ± 0.5 |  |

EXAMPLE 33

Production of soft capsules 1 mg of Compound (148) was dissolved in 60 g of fractionated coconut oil and soft capsules were produced by use of a soft gelatin capsule making machine, each capsule being made to contain 1 $\mu$g of Compound (148).

EXAMPLE 34

Production of powder

A powder was prepared in accordance with the following formulation.

| Active ingredient | 10 $\mu$g |
|---|---|
| Lactose | 100 mg |
| Corn starch | 100 mg |
| Hydroxypropyl cellulose | 10 mg |
|  | 210 mg |

The active ingredient, lactose and corn starch were mixed, and an aqueous solution of hydroxypropyl cellulose was added. The mixture was dried to form a dust powder.

Compound (142) was used typically as the active ingredient.

What is claimed is:

1. A 4-hydroxy-2-cyclopentenone represented by the following formula (I)

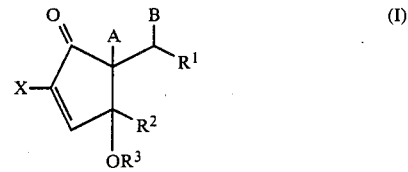

wherein X represents a hydorgen or halogen atom, A represents a hydrogen atom and B represents a hydroxyl group, or A and B are bonded to each other to represent a bond, $R^1$ represents a substituted or unsubstituted alkyl, alkenyl or alkynyl group having 1 to 10 carbon atoms, $R^2$ represents a substituted or unsubstituted alkyl grop having 1 to 10 carbon atoms, and wherein the substituents on the group $R^1$ and $R^2$ may be identical or different from each other and are selected from a group of the formula —COOR$^4$ in which $R^4$ represents a hydrogen atom, an alkyl group having 1 to 10 carbon atoms or one equivalent of a cation; a group of the formula —OR$^5$ in which $R^5$ represents a hydrogen atom, an alkyl group having 1 to 6 carbon atoms which may be substituted by a halogen atom, a carboacyl group having 1 to 7 carbon atoms, or a phenyl group, the phenyl group being optionally substituted by a halogen atom, an alkyl group having 1 to 4 carbon atoms or an alkoxy group having 1 to 4 carbon atoms; a phenyl group which may be substituted by a halogen atom, an alkyl group having 1 to 4 carbon atoms or an alkoxy group having 1 to 4 carbon atoms; a cycloalkyl group having 3 to 8 carbon atoms which may be substituted by a halogen atom, an alkyl group having 1 to 4 carbon atoms or an alkoxy group having 1 to 4 carbon atoms; or a residue or a carbohydrate, and $R^3$ represents a hydrogen atom, a carboacyl group having 2 to 7 carbon atoms, a tri($C_1$-$C_7$)hydrocarbonsilyl group, or a group forming an acetal linkage together with the oxygen atom of the hydroxyl group.

2. The 4-hydroxy-2-cyclopentenone of claim 1 which is represented by the following formula (I)-a

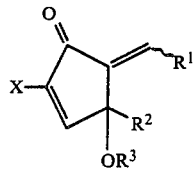
(I)-a wherein X, $R^1$, $R^2$ and $R^3$ are as defined above.

3. The 4-hydroxy-2-cyclopentenone of claim 1 which is represented by the following formula (I)-b

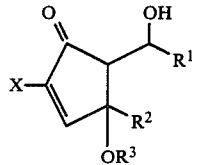
(I)-b

4. The 4-hydroxy-2-cyclopentenone of claim 1 wherein X in formula (I) is a chlorine atom.

5. The 4-hydroxy-2-cyclopentenone of claim 1 which is represented by the following formula (I)′

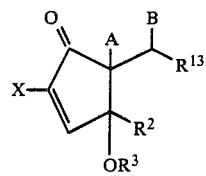
(I)′ wherein X, A, B, $R^2$ and $R^3$ are as defined above, and $R^{13}$ represents a substituted or unsubstituted alkyl group having 1 to 10 carbon atoms.

6. The 4-hydroxy-2-cyclopentenone of claim 1 which is represented by the following formula (I)″

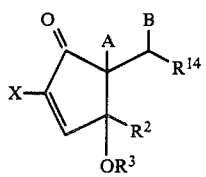
(I)″ wherein X, A, B, $R^2$ and $R^3$ are as defined above, and $R^{14}$ represents a substituted or unsubstituted $C_2$–$C_{10}$ alken-1-yl group having a carbon-carbon double bond at least at the 1-position.

7. A pharmaceutical composition comprising a pharmaceutically effective amount of a least one 4-hydroxy-2cyclopentenone of claim 1 and a pharmaceutically acceptable carrier.

8. The pharmaceutical composition of claim 7 which is for the treatment of malignant tumors.

9. Use of the 4-hydroxy-2-cylopentenone of claim for the treatment of malignant tumors.

* * * * *